(12) United States Patent
Russell et al.

(10) Patent No.: US 11,147,603 B2
(45) Date of Patent: *Oct. 19, 2021

(54) BONE SCREWS AND METHODS OF USE THEREOF

(71) Applicant: Innovision, Inc., Memphis, TN (US)

(72) Inventors: Thomas A Russell, Memphis, TN (US); Todd A Glover, Memphis, TN (US); Samuel A Houston, Memphis, TN (US); John R Pepper, Memphis, TN (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 369 days.

This patent is subject to a terminal disclaimer.

(21) Appl. No.: 15/907,982

(22) Filed: Feb. 28, 2018

(65) Prior Publication Data

US 2018/0185077 A1 Jul. 5, 2018

Related U.S. Application Data

(63) Continuation of application No. 15/091,696, filed on Apr. 6, 2016, now Pat. No. 9,936,992, which is a continuation of application No. 14/044,450, filed on Oct. 2, 2013, now Pat. No. 9,333,018, which is a continuation of application No. 12/556,246, filed on Sep. 9, 2009, now Pat. No. 8,574,273.

(51) Int. Cl.
*A61B 17/86* (2006.01)
*A61B 17/04* (2006.01)
(Continued)

(52) U.S. Cl.
CPC ........ *A61B 17/864* (2013.01); *A61B 17/0401* (2013.01); *A61B 17/7098* (2013.01);
(Continued)

(58) Field of Classification Search
CPC .................................................... A61B 17/864
See application file for complete search history.

(56) References Cited

U.S. PATENT DOCUMENTS 2,414,882 A 1/1947 Longfellow
2,570,465 A 10/1951 Lundholm
(Continued)

FOREIGN PATENT DOCUMENTS

AU 2011218783 A1 10/2011
AU 2011218783 B2 4/2015
(Continued)

OTHER PUBLICATIONS

"Canadian Application Serial No. 2,750,254, Response filed Jun. 12, 2018 to Office Action dated Dec. 13, 2017", 20 pgs.
(Continued)

*Primary Examiner* — Samuel S Hanna
(74) *Attorney, Agent, or Firm* — Schwegman Lundberg & Woessner, P.A.

(57) ABSTRACT

The invention features bone screws having a threaded screw body and a screw head attached to one end of the screw body, the bone screw further including: a) an interior channel extending longitudinally through the screw head and through at least a portion of the screw body, wherein the interior channel has a width of less than 5.0 millimeters; and b) a plurality of radially-disposed delivery channels connecting the interior channel to the exterior of the screw body, each delivery channel having exterior openings. The invention further features devices that include a bone screw and a delivery manifold detachably attached to the screw head of the bone screw. In addition, the invention features methods of treating a patient having a bone defect by using a bone screw described herein.

18 Claims, 33 Drawing Sheets

(51) Int. Cl.
*A61B 17/70* (2006.01)
*A61B 17/80* (2006.01)
*A61B 17/88* (2006.01)
*A61C 8/00* (2006.01)
*A61C 8/02* (2006.01)
*A61B 17/56* (2006.01)

(52) U.S. Cl.
CPC .......... *A61B 17/80* (2013.01); *A61B 17/8057* (2013.01); *A61B 17/8605* (2013.01); *A61B 17/8811* (2013.01); *A61B 17/8875* (2013.01); *A61C 8/0022* (2013.01); *A61B 17/861* (2013.01); *A61B 2017/044* (2013.01); *A61B 2017/561* (2013.01); *A61C 8/0006* (2013.01)

(56) References Cited

U.S. PATENT DOCUMENTS

| | | | |
|---|---|---|---|
| 3,554,193 A | 1/1971 | Konstantinou et al. | |
| 4,479,271 A | 10/1984 | Bolesky et al. | |
| 4,494,535 A | 1/1985 | Haig | |
| 4,640,271 A | 2/1987 | Lower | |
| 4,653,489 A | 3/1987 | Tronzo | |
| 4,756,307 A | 7/1988 | Crowninshield | |
| 4,781,181 A | 11/1988 | Tanguy | |
| 4,860,513 A | 8/1989 | Whitman | |
| 4,950,270 A | 8/1990 | Bowman et al. | |
| RE33,348 E | 9/1990 | Lower | |
| 5,019,079 A | 5/1991 | Ross | |
| 5,047,030 A | 9/1991 | Draenert | |
| 5,122,141 A | 6/1992 | Simpson et al. | |
| 5,129,901 A | 7/1992 | Decoste | |
| 5,143,498 A | 9/1992 | Whitman | |
| 5,147,406 A | 9/1992 | Houston et al. | |
| 5,152,792 A | 10/1992 | Watkins et al. | |
| 5,156,606 A | 10/1992 | Chin | |
| 5,167,664 A | 12/1992 | Hodorek | |
| 5,169,400 A | 12/1992 | Muhling et al. | |
| 5,180,382 A | 1/1993 | Frigg et al. | |
| 5,190,551 A | 3/1993 | Chin et al. | |
| 5,192,282 A | 3/1993 | Draenert | |
| 5,209,805 A | 5/1993 | Spraggins | |
| 5,214,987 A | 6/1993 | Fenton, Sr. | |
| 5,222,957 A | 6/1993 | Mccoll et al. | |
| 5,222,958 A | 6/1993 | Chin | |
| 5,249,899 A | 10/1993 | Wilson | |
| 5,324,292 A | 6/1994 | Meyers | |
| 5,334,204 A | 8/1994 | Clewett et al. | |
| 5,338,197 A | 8/1994 | Kwan | |
| 5,344,654 A | 9/1994 | Rueger et al. | |
| 5,354,557 A | 10/1994 | Oppermann et al. | |
| 5,383,878 A | 1/1995 | Roger et al. | |
| 5,391,181 A | 2/1995 | Johnson et al. | |
| 5,484,440 A | 1/1996 | Allard | |
| 5,484,445 A | 1/1996 | Knuth | |
| 5,489,143 A | 2/1996 | Adachi et al. | |
| 5,496,319 A | 3/1996 | Allard et al. | |
| 5,534,027 A | 7/1996 | Hodorek | |
| 5,534,032 A | 7/1996 | Hodorek | |
| 5,536,127 A | 7/1996 | Pennig et al. | |
| 5,573,548 A | 11/1996 | Nazre et al. | |
| 5,601,559 A | 2/1997 | Melker et al. | |
| 5,649,931 A | 7/1997 | Bryant et al. | |
| 5,658,285 A | 8/1997 | Marnay et al. | |
| 5,725,581 A * | 3/1998 | Brånemark | A61F 2/30749 606/304 |
| 5,743,912 A | 4/1998 | Lahille et al. | |
| 5,783,217 A | 7/1998 | Lee et al. | |
| 5,788,702 A | 8/1998 | Draenert | |
| 5,854,207 A | 12/1998 | Lee et al. | |
| 5,938,664 A | 8/1999 | Winquist et al. | |
| 6,016,727 A | 1/2000 | Morgan | |
| 6,027,742 A | 2/2000 | Lee et al. | |
| 6,036,491 A | 3/2000 | Hansson | |
| 6,048,343 A | 4/2000 | Mathis et al. | |
| 6,210,376 B1 | 4/2001 | Grayson | |
| 6,214,012 B1 | 4/2001 | Karpman et al. | |
| 6,214,368 B1 | 4/2001 | Lee et al. | |
| 6,287,341 B1 | 9/2001 | Lee et al. | |
| 6,319,270 B1 | 11/2001 | Grafton et al. | |
| 6,331,312 B1 | 12/2001 | Lee et al. | |
| 6,436,100 B1 | 8/2002 | Berger | |
| 6,440,136 B1 | 8/2002 | Gambale et al. | |
| 6,541,037 B1 | 4/2003 | Lee et al. | |
| 6,565,572 B2 | 5/2003 | Chappius | |
| 6,604,945 B1 | 8/2003 | Jones | |
| 6,610,079 B1 | 8/2003 | Li et al. | |
| 6,635,059 B2 | 10/2003 | Randall et al. | |
| 6,682,531 B2 | 1/2004 | Winquist et al. | |
| 6,755,835 B2 | 6/2004 | Schultheiss et al. | |
| 6,863,671 B1 | 3/2005 | Strobel et al. | |
| 6,875,218 B2 | 4/2005 | Dye et al. | |
| 6,875,237 B2 | 4/2005 | Dye et al. | |
| 6,890,335 B2 | 5/2005 | Grabowski et al. | |
| 6,893,447 B2 | 5/2005 | Dominguez et al. | |
| 6,918,912 B2 | 7/2005 | Seemann | |
| 6,953,594 B2 | 10/2005 | Lee et al. | |
| 6,962,593 B2 | 11/2005 | Sanford et al. | |
| 6,972,130 B1 | 12/2005 | Lee | |
| 6,989,014 B2 | 1/2006 | Justin et al. | |
| 7,011,664 B2 | 3/2006 | Haney | |
| 7,037,309 B2 | 5/2006 | Weil et al. | |
| 7,150,879 B1 | 12/2006 | Lee et al. | |
| 7,198,627 B2 | 4/2007 | Bagga et al. | |
| 7,258,692 B2 | 8/2007 | Thelen et al. | |
| 7,261,716 B2 | 8/2007 | Strobel et al. | |
| 7,300,439 B2 | 11/2007 | May | |
| 7,306,605 B2 | 12/2007 | Ross | |
| 7,316,687 B2 | 1/2008 | Aikins et al. | |
| 7,318,841 B2 | 1/2008 | Tofighi et al. | |
| 7,328,131 B2 | 2/2008 | Donofrio et al. | |
| 7,335,201 B2 | 2/2008 | Doubler et al. | |
| 7,338,493 B1 | 3/2008 | Vandewalle | |
| 7,354,442 B2 | 4/2008 | Sasso et al. | |
| 7,488,320 B2 | 2/2009 | Middleton | |
| 7,517,539 B1 | 4/2009 | Lee et al. | |
| 7,520,880 B2 | 4/2009 | Claypool et al. | |
| 7,608,097 B2 | 10/2009 | Kyle | |
| 7,637,929 B2 | 12/2009 | Auth | |
| 7,717,947 B1 * | 5/2010 | Wilberg | A61B 17/864 606/304 |
| 7,731,738 B2 | 6/2010 | Jackson et al. | |
| 7,892,265 B2 | 2/2011 | Perez-cruet et al. | |
| 7,951,179 B2 | 5/2011 | Matityahu | |
| 8,231,632 B1 | 7/2012 | Jordan et al. | |
| 8,574,273 B2 | 11/2013 | Russell et al. | |
| 9,333,018 B2 | 5/2016 | Russell et al. | |
| 9,936,992 B2 | 4/2018 | Russell et al. | |
| 2001/0021852 A1 | 9/2001 | Chappius | |
| 2003/0045881 A1 * | 3/2003 | Barouk | A61B 17/863 606/304 |
| 2004/0015172 A1 * | 1/2004 | Biedermann | A61B 17/8685 606/304 |
| 2004/0225292 A1 | 11/2004 | Sasso et al. | |
| 2005/0015061 A1 | 1/2005 | Sweeney | |
| 2005/0021084 A1 | 1/2005 | Lu et al. | |
| 2005/0055026 A1 * | 3/2005 | Biedermann | A61B 17/1659 606/278 |
| 2005/0107800 A1 | 5/2005 | Frankel et al. | |
| 2006/0247642 A1 | 11/2006 | Stone et al. | |
| 2009/0018590 A1 * | 1/2009 | Dorawa | A61B 17/864 606/301 |
| 2011/0060373 A1 | 3/2011 | Russell et al. | |
| 2014/0031791 A1 | 1/2014 | Russell et al. | |
| 2016/0220291 A1 | 8/2016 | Russell et al. | |

FOREIGN PATENT DOCUMENTS

| | | |
|---|---|---|
| CA | 1227902 A | 10/1987 |
| CA | 2057957 A1 | 6/1992 |
| CA | 2062012 A1 | 9/1992 |
| CA | 2076501 A1 | 3/1993 |
| CA | 2109850 A1 | 5/1994 |

(56) References Cited

FOREIGN PATENT DOCUMENTS

| | | |
|---|---|---|
| CA | 2243086 A1 | 8/1997 |
| CA | 2289152 A1 | 5/2000 |
| CA | 2394072 A1 | 6/2001 |
| CA | 2405127 A1 | 10/2001 |
| CA | 2405782 A1 | 10/2001 |
| CA | 2413325 A1 | 1/2002 |
| CA | 2417662 A1 | 2/2002 |
| CA | 2449354 A1 | 7/2002 |
| CA | 2405230 A1 | 10/2002 |
| CA | 2390912 A1 | 1/2003 |
| CA | 2062012 C | 4/2003 |
| CA | 2407108 A1 | 4/2003 |
| CA | 2506653 A1 | 6/2003 |
| CA | 2524797 A1 | 11/2004 |
| CA | 2467262 A1 | 12/2004 |
| CA | 2109850 C | 1/2005 |
| CA | 2626145 A1 | 5/2007 |
| CA | 2243086 C | 6/2007 |
| CA | 2405230 C | 11/2007 |
| CA | 2390912 C | 1/2008 |
| CA | 2467262 C | 7/2008 |
| CA | 2394072 C | 8/2008 |
| CA | 2405782 C | 8/2008 |
| CA | 2449354 C | 5/2009 |
| CA | 2407108 C | 1/2010 |
| CA | 2405127 C | 2/2010 |
| CA | 2736891 A1 | 3/2010 |
| CA | 2742077 A1 | 5/2010 |
| CA | 2744392 A1 | 6/2010 |
| CA | 2506653 C | 4/2011 |
| DE | 2818254 A1 | 10/1979 |
| DE | 3434807 A1 | 12/1985 |
| DE | 19540180 A1 | 5/1996 |
| DE | 19949285 A1 | 5/2001 |
| DE | 10246386 A1 | 4/2004 |
| EP | 0172130 A2 | 2/1986 |
| EP | 0451932 A1 | 10/1991 |
| FR | 2744010 A1 | 8/1997 |
| JP | 751292 A | 2/1995 |
| JP | 07222752 A | 8/1995 |
| JP | 10211213 A | 8/1998 |
| WO | WO-8806023 A1 | 8/1988 |
| WO | WO-8909030 A1 | 10/1989 |
| WO | WO-0117447 A1 | 3/2001 |
| WO | WO-0126568 A1 | 4/2001 |

OTHER PUBLICATIONS

"German Application Serial No. 102011112890.9, Response filed Jan. 8, 2018 to Office Action dated Sep. 26, 2017", 37 pgs.

"Canadian Application Serial No. 2,750,254, Office Action dated Dec. 13, 2017", 5 pgs.

"U.S. Appl. No. 12/556,246, Advisory Action dated Jul. 18, 2013", 3 pgs.

"U.S. Appl. No. 12/556,246, Examiner Interview Summary dated Jan. 31, 2013", 3 pgs.

"U.S. Appl. No. 12/556,246, Examiner Interview Summary dated Aug. 8, 2013", 3 pgs.

"U.S. Appl. No. 12/556,246, Final Office Action dated Apr. 5, 2013", 16 pgs.

"U.S. Appl. No. 12/556,246, Non Final Office Action dated Aug. 31, 2012", 11 pgs.

"U.S. Appl. No. 12/556,246, Notice of Allowance dated Sep. 13, 2013", 11 pgs.

"U.S. Appl. No. 12/556,246, Response filed Jan. 31, 2013 to Non Final Office Action dated Aug. 31, 2012", 14 pgs.

"U.S. Appl. No. 12/556,246, Response filed May 17, 2012 to Restriction Requirement dated Apr. 20, 2012", 2 pgs.

"U.S. Appl. No. 12/556,246, Response filed Jul. 5, 2013 to Final Office Action dated Apr. 5, 2013", 27 pgs.

"U.S. Appl. No. 12/556,246, Response filed Aug. 1, 2013 to Advisory Action dated Jul. 18, 2013", 13 pgs.

"U.S. Appl. No. 12/556,246, Response filed Aug. 14, 2012 to Restriction Requirement dated Jul. 19, 2012", 13 pgs.

"U.S. Appl. No. 12/556,246, Restriction Requirement dated Apr. 20, 2012", 9 pgs.

"U.S. Appl. No. 12/556,246, Restriction Requirement dated Jul. 19, 2012", 7 pgs.

"U.S. Appl. No. 14/044,450, Notice of Allowance dated Jan. 13, 2016", 17 pgs.

"U.S. Appl. No. 14/044,450, Response filed Dec. 9, 2015 to Restriction Requirement dated Oct. 9, 2015", 7 pgs.

"U.S. Appl. No. 14/044,450, Restriction Requirement dated Oct. 9, 2015", 8 pgs.

"U.S. Appl. No. 15/091,696, Corrected Notice of Allowance dated Dec. 15, 2017", 13 pgs.

"U.S. Appl. No. 15/091,696, Notice of Allowance dated Nov. 29, 2017", 16 pgs.

"U.S. Appl. No. 15/091,696, Response filed Oct. 25, 2017 to Restriction Requirement dated Aug. 30, 2017", 9 pgs.

"U.S. Appl. No. 15/091,696, Restriction Requirement dated Aug. 30, 2017", 10 pgs.

"Australian Application Serial No. 2011218783, Examination Report dated Oct. 25, 2013", 4 pgs.

"Australian Application Serial No. 2011218783, Examination Report dated Dec. 8, 2014", 3 pgs.

"Australian Application Serial No. 2011218783, Response filed Mar. 4, 2015 to Examination Report dated Dec. 8, 2014", 13 pgs.

"Australian Application Serial No. 2011218783, Response filed Oct. 24, 2014 to Examination Report dated Oct. 25, 2013", 19 pgs.

"Canadian Application Serial No. 2,750,254, Office Action dated Apr. 1, 2016", 3 pgs.

"Canadian Application Serial No. 2,750,254, Response filed Sep. 7, 2017 to Office Action dated Apr. 1, 2016", 19 pgs.

"German Application Serial No. 102011112890.9, Office Action dated Apr. 16, 2012", 2 pgs.

"German Application Serial No. 102011112890.9, Office Action dated May 8, 2015", w/English Translation, 12 pgs.

"German Application Serial No. 102011112890.9, Office Action dated Sep. 26, 2017", w/ summary in English, 10 pgs.

"German Application Serial No. 102011112890.9, Response filed May 10, 2012 to Office Action dated Apr. 16, 2012", 35 pgs.

"International Application Serial No. PCT/US2014/020678, International Search Report dated Jun. 23, 2014", 3 pgs.

"International Application Serial No. PCT/US2014/020678, Written Opinion dated Jun. 23, 2014", 6 pgs.

"Innovision, Inc. 510 (k) Summary", K102528, (Jul. 28, 2011), 5 pgs.

Chappuis, et al., "Fixation Strength Studies with Fenestrated Cemented Pedicle Screws in Human Cadaver", Poster Exhibit, Sixteenth Annual Meeting North American Spine Society, Seattle, WA, (Oct. 2001), 4 pgs.

Dickman, CA, et al., "Cannulated Screws for Odontoid Screw Fixation and Atlantoaxial Transarticular Screw Fixation. Technical Note.", J. Neurosurg. 83(6),1095-100, Abstract Only, (Dec. 1995), 1 pg.

Trumble, et al., "Displaced Scaphoid Fractures Treated With Open Reduction and Internal Fixation With a Cannulated Screw", The Journal of Bone and Joint Surgery; vol. 82-A, No. 5, (May 2000), 633-641.

Tsuchiya, et al., "Cannulation of Simple Bone Cysts", J. Bone Joint Surg. Am. 84, (2002), 245-248.

* cited by examiner

12

BONE SCREWS AND METHODS OF USE THEREOF

CLAIM OF PRIORITY

This application is a continuation of U.S. patent application Ser. No. 15/091,696, filed on Apr. 6, 2016, which is a continuation of U.S. patent application Ser. No. 14/044,450, filed on Oct. 2, 2013, now issued as U.S. Pat. No. 9,333,018, which is a continuation of U.S. patent application Ser. No. 12/556,246, filed on Sep. 9, 2009, now issued as U.S. Pat. No. 8,574,273, the benefit of priority of each of which is claimed hereby, and each of which are incorporated by reference herein in its entirety.

FIELD OF THE INVENTION

The invention relates to devices, in particular, bone screws, and methods of use thereof for the treatment of bone defects.

BACKGROUND OF THE INVENTION

Fixation tools and devices, which are available in a wide variety of different shapes and sizes, have long been used in the repair of bone defects, such as bone fractures. A physician typically sets the bone to be repaired in the proper position and then uses the fixation tools and devices to secure the bone in that position during the healing process.

A fixation device, such as a bone plate or rod, can be secured to the bone by a fixation tool, such as a bone screw. Alternatively, a bone screw can be used by itself to repair a bone defect. One drawback associated with prior art bone screws is the potential for the bone screw to back out after implantation. To inhibit back out, bone screws have been modified with various thread designs and locking features, with some success.

When installing a bone anchor or screw, a surgeon will typically tap a hole, remove the tap and then install the screw into the hole while maintaining the alignment of the bone with another bone or prosthesis. The bone screw can be secured in the bony bed by filling the hole before installation of the screw with a bone cement, such as polymethylmethacrylate or other fillable and flowable materials.

The use of a solid screw with a bone cement or other fillable material may increase the initial stiffness and strength of the repair, but may not significantly decrease loosening of the screw at the repair site. The substitution of solid screws with cannulated screws that can extrude a bone cement or other fillable material may improve the strength of the repair while at the same time reducing the likelihood that the screw will loosen and pull out, but distribution of the bone cement or fillable material through the screw and throughout the repair site remains a problem. Thus, there remains a need for a cannulated bone screw for use with a bone cement or fillable material that is capable of securing bone at a repair site while also preventing loosening and pull-out of the bone screw following the repair.

SUMMARY OF THE INVENTION

In general, the invention features bone screws, devices incorporating the bone screws, and methods of treating a patient having a bone defect by using bone screws as described herein.

Accordingly, in a first aspect, the invention features a bone screw that includes a threaded screw body and a screw head attached to one end of the screw body; the bone screw further includes a) an interior channel extending longitudinally through the screw head and through at least a portion of the screw body (e.g., through substantially the full length of the screw body or through only one-half, one-third, or less of the length of the screw body), wherein the interior channel has a width of less than 5.0 millimeters (mm), e.g., less than or equal to about 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, or 5.0 mm, or wherein the width is in a range spanning any of the preceding values, e.g., 0.4 to 5.0 mm, 0.5 to 4.0 mm, 0.8 to 3.5 mm, 1.0 to 3.2 mm, 1.2 to 2.5 mm, or 1.6 to 2.0 mm; and b) a plurality of radially-disposed delivery channels connecting the interior channel to the exterior of the screw body. In several embodiments, the interior channel is substantially cylindrical, decreases in width (where the terms "width" and "diameter" are used synonymously in the context of a substantially cylindrical interior channel) along a direction distal to the screw head, decreases substantially linearly as a function of longitudinal distance from the screw head, or has a width that decreases in step-wise fashion. In another embodiment, the delivery channels of the bone screw have exterior openings of varying cross-sectional areas. In another embodiment, the exterior openings are positioned along the length of the screw body. In an embodiment, the exterior openings are positioned between the threads of the screw body (e.g., between alternating threads of the screw body or each thread of the screw body). In other embodiments, the exterior openings are i) arrayed in increasing cross-sectional area along a direction distal to the screw head, or ii) positioned at substantially equal intervals along at least a portion of the screw body, or iii) may be substantially circular, substantially slot-shaped, substantially square, substantially polygonal, or combinations thereof (e.g., the delivery channels may include substantially circular and substantially slot-shaped exterior openings). In yet other embodiments, the delivery channels are sized to generate substantially equal flow rates of a flowable medium (e.g., a bone void filler material, a cement (e.g., polymethacrylate (PMA), polymethylmethacrylate (PMMA), calcium phosphate, or calcium sulfate), or a pharmaceutical agent) extruded through each of the delivery channels following introduction of the flowable medium through the screw head into the interior channel. In an embodiment, the cement may be a paste, putty, or slurry. In other embodiments, the cement hardens in less than 2 hours, 1 hour, 30 minutes, 15 minutes, 10 minutes, or 5 minutes.

In other embodiments of the bone screw of the first aspect of the invention, each delivery channel is substantially cylindrical or tapered along at least a portion of its radial axis. In yet another embodiment, the delivery channels are disposed at more than one angular orientation with respect to the longitudinal axis of the screw body. In yet other embodiments, for each of the delivery channels, i) an additional delivery channel and exterior opening is positioned at substantially the same longitudinal distance from the screw head and is positioned substantially 180 degrees apart around the longitudinal axis of the screw body, or ii) two additional delivery channels and exterior openings are positioned at substantially the same longitudinal distance from the screw head and are positioned substantially 120 degrees apart around the longitudinal axis of the screw body, or iii) three additional delivery channels and exterior openings are positioned at substantially the same longitudinal distance from the screw head and are positioned substantially 90 degrees apart around the longitudinal axis of the screw body.

In other embodiments of the first aspect of the invention, the bone screw body further includes at least one exterior groove (e.g., the groove(s) can be substantially straight or substantially helical) extending along at least a portion of the exterior of the screw body and connecting at least a subset of the exterior openings of the delivery channels. In an embodiment, the depth of the exterior groove(s) is less than the depth of the delivery channels. In other embodiments, the screw body further includes a plurality of exterior grooves (e.g., two exterior grooves on substantially opposite sides of the screw body, three substantially equidistant exterior grooves, or four exterior grooves, in which each adjacent pair of the exterior grooves is substantially equidistant), each extending along at least a portion of the exterior of the screw body and connecting at least a subset of the exterior openings of the delivery channels, wherein the depth of each of the exterior groove is less than the depth of each said delivery channel. In other embodiments, the depth of each of the grooves, relative to the major diameter of the bone screw, is between 0.1 mm and 1.0 mm. In another embodiment, the plurality of exterior grooves is of substantially identical shape. In other embodiments, the exterior openings i) range in cross-sectional area from 0.1 $mm^2$ to 12 $mm^2$ or ii) are substantially circular and range in diameter from 0.1 mm to 4 mm.

In yet other embodiments of the first aspect of the invention, the bone screw includes between 1 and 200 delivery channels, e.g., 1, 5, 10, 20, 30, 40, 50, 60, 70, 80, 90, 100, 125, 150, 175, or 200, or a range spanning any of the preceding values. In another embodiment, the delivery channels are substantially cylindrical. In yet other embodiments, the length of the screw body is between about 10 mm and 200 mm (e.g., between about 20 and 100 mm in length), the major diameter of the screw body is between about 0.5 mm and 20 mm (e.g., between about 2 and 10 mm in diameter), the threads of the screw body are spaced between about 0.05 mm and 500 mm apart (e.g., between about 0.5 mm to 250 mm apart), the radial height of the threads is between about 0.1 mm and 20 mm (e.g., between about 2 and 10 mm), the diameter of the screw head is between about 3 mm and 30 mm (e.g., between about 5 and 20 mm), and the height of the screw head is between about 1 mm and 25 mm (e.g., between about 5 and 15 mm).

With reference to any bone screw dimensions described herein, larger or smaller bone screws that scale proportionally in some or all dimensions are also contemplated, as well as larger or smaller bone screws that do not scale proportionally. Generally, the dimensions of a bone screw to be used in a surgical procedure are selected in accordance with the size of the bone or bones being treated.

In yet other embodiments of the first aspect of the invention, the bone screw is made of a material selected from stainless steel alloy, titanium alloy, commercially pure titanium, cobalt chrome, polyetheretherketone, and calcium phosphate, or combinations thereof. In addition, the bone screw may further include a sealable polymeric barrier (e.g., a silicone elastomer, such as a Silastic® brand silicone elastomer (Dow Corning) or a cross-linked polydimethylsiloxane material) that closes off the driving end of the bone screw from the external environment surrounding the bone screw to form a reserveroir space. The reservoir space may be filled with a flowable medium that may include, e.g., a pharmaceutical agent, which may distribute evenly along the bone over time. In an embodiment, the sealable polymeric barrier is a silicone elastomer. In another embodiment, the pharmaceutical reservoir has a volume capacity of between about 0.2 ml and 20 ml.

In yet other embodiments, the screw head is i) machined to fit a delivery manifold capable of introducing a flowable medium to the bone screw, or ii) machined to fit a rotational driver that is inserted within the manifold, or iii) is hollow, or iv) is threaded, or v) is machined to be driven by a spanner, or vi) includes a hexagonal opening, a Robertson opening, a slotted opening, a Phillips opening, a Torx opening, a triple square opening, a polydrive opening, a one-way clutch opening, a spline drive opening, a double hex opening, or a Bristol opening, or vii) is substantially circular, substantially hexagonal, substantially square, or substantially polygonal.

In yet another embodiment, the bone screw further includes an internal plug that fully or partially occludes the interior channel within the screw body and that is stationary within, or slidably movable along, the interior channel. In other embodiments, the plug is positioned at the hollow tip of a fully cannulated screw to prevent escape of flowable medium from the tip, or it is positioned on, in, or close to the screw head in order to prevent escape of flowable medium from the screw head or entry of other substances into the screw head and interior channel. The plug can be placed entirely inside the interior channel, or it can screw into place within the screw head and extend a designated distance into the interior channel. The plug can be designed to occlude all, or any subset of, delivery channels (e.g., 1, 2, 5, 10, 20, 30, 50, or more delivery channels).

In other embodiments, the plug is pre-filled (e.g., prior to insertion of the internal plug into the bone screw, prior to implantation of the bone screw into a patient, or prior to extrusion of a flowable medium (e.g., bone cement) through the internal channel of the bone screw) with, e.g., a flowable medium (e.g., polyethylene, metal alloy, bone void filler material, cement, or a pharmaceutical agent) that is capable of releasing by fluid dissolution from the plug.

In a second aspect, the invention features a device that includes the bone screw of the first aspect of the invention and a delivery manifold detachably attached to the outside of the screw head. In an embodiment, the delivery manifold and the screw head have complementary threaded regions that allow attachment to each other. In another embodiment, the device further includes a rotational driver that engages with the screw head, thereby allowing for rotation of the bone screw about its longitudinal axis by rotation of the driver. In yet other embodiments, the device is capable of receiving a flowable medium (e.g., a bone void filler material, cement, or a pharmaceutical agent) through the delivery manifold and the bone screw is capable of being tightened, prior to hardening of the flowable medium, by the steps of i) inserting the rotational driver through the flowable medium within the delivery manifold; ii) engaging the screw head with an end of the rotational driver; and iii) tightening the bone screw into final position by rotating the rotational driver. In another embodiment, the device is capable of being tightened by the steps of i) inserting the rotational driver through the delivery manifold; ii) engaging the screw head with an end of the rotational driver; and iii) tightening the bone screw into final position by rotating the rotational driver. Following removal of the rotational driver, a flowable medium is added to the delivery manifold and injected into the bone screw through the screw head and into the interior channel by applying pressure at the proximal end of the delivery manifold (e.g., by depressing a plunger from the proximal end to the distal end through the delivery manifold towards the screw head). Alternatively, the bone screw is capable of being tightened by i) inserting the rotational driver through flowable medium already present within the delivery manifold; ii) engaging the screw head with the end of the rotational driver; and iii) tightening the bone screw into final position by rotating the rotational driver. In an embodiment, the delivery manifold includes a Luer lock, e.g., allowing for attachment of a syringe that can be operated using manual pressure.

In a third aspect, the invention features a device that includes a) a bone screw (e.g., a bone screw of the first aspect of the invention) having a threaded screw body and a screw head attached to one end of the screw body, in which the bone screw further includes: i) an interior channel extending longitudinally through the screw head and through at least a portion of the screw body; and ii) a radially-disposed delivery channel connecting the interior channel to the exterior of said screw body; and b) a delivery manifold attached to the screw head, in which the delivery manifold is configured to receive a rotational driver within the interior of the delivery manifold. An end of the rotational driver is configured to engage with the screw head and the screw head is machined to connect with the rotational driver.

In an embodiment, the delivery manifold is removable and is detachably attached to the outside of the screw head. In other embodiments, the delivery manifold is i) connected to the interior of the screw head or ii) is connected to the screw head via a butt joint connection (e.g., using a slidable piece of material to bridge the screw head and delivery manifold). In another embodiment, the device is capable of receiving a flowable medium (e.g., a bone void filler material, cement, or a pharmaceutical agent) through the delivery manifold, and the bone screw is capable of being tightened, prior to hardening of the flowable medium. For example, the bone screw is capable of being tightened by inserting the rotational driver through the delivery manifold; ii) engaging the screw head with an end of the rotational driver; and iii) tightening the bone screw into final position by rotating the rotational driver. Following removal of the rotational driver, a flowable medium may be added to the delivery manifold and injected into the bone screw through the screw head and into the interior channel by applying pressure at the proximal end of the delivery manifold (e.g., by depressing a plunger from the proximal end to the distal end through the delivery manifold towards the screw head).

Alternatively, the bone screw is capable of being tightened by i) inserting the rotational driver through flowable medium already present within the delivery manifold; ii) engaging the screw head with the end of the rotational driver; and iii) tightening the bone screw into final position by rotating the rotational driver. In an embodiment, the delivery manifold includes a Luer lock.

A fourth aspect of the invention features a method of making the bone screw of the first aspect of the invention. In an embodiment, the bone screw is made using an extrude hone process that may involve, e.g., extrusion of adhesive putty under high pressure to provide internal venture, which provides internal edge breaks in the bone screw in areas not accessible to conventional machining techniques.

A fifth aspect of the invention features a method of treating a patient having a bone defect (e.g., subarticular fracture, a defect of the spine or vetebra, or a defect of the radius, ulna, fibula, clavicle, humerus, pelvis, femur, patella, tibia, talus, calcaneus, navicular, cuneiforms, metatarsals, metacarpals, phalanges, scapula, ankle, teeth, or mandible) by a) positioning the bone screw or device of the first, second, or third aspects of the invention in proximity to the bone defect (e.g., positioning the bone screw so that it contacts the intraosseous space of a bone); b) introducing a flowable medium (e.g., a bone void filler material, cement, or a pharmaceutical agent) into the interior channel of the bone screw; c) allowing the flowable medium to be extruded through the delivery channels (e.g., the flowable medium is extruded through substantially all or a plurality of the delivery channels, e.g., in substantially equal volumes), and d) allowing the flowable medium to harden, thereby fixing the bone screw in place. In an embodiment, the method involves maxillomandibular or craniofacial fixation, temporary fixation for repairing a bone defect in a staged reconstruction, glenoid or humeral fixation, patellar fixation, or spine fixation. In other embodiments, the bone screw is placed within a pedicle, used to anchor an interbody device, used to anchor spinal fusion plates and spacer replacement, used in an osteoporotic vertebra, or positioned in proximity to the spinous processes of adjacent vertebrae. In yet other embodiments, the method includes the insertion of a rod, pin, nail, or bone plate in proximity to the bone defect. In another embodiment, the method involves, prior to step b), fluidically coupling the screw head to a delivery manifold capable of introducing the flowable medium to the interior channel of the bone screw. In still another embodiment, the method further includes introducing the flowable medium to the interior channel of the bone screw through the delivery manifold. Furthermore, prior to step d), the method further involves i) inserting a rotational driver through the flowable medium within said delivery manifold; ii) engaging the screw head with the rotational driver; and iii) tightening the bone screw into final position by rotating the rotational driver.

In a sixth aspect, the invention features a kit that includes one or more bone screws of the first aspect of the invention, the device of the second or third aspect of the invention and, optionally, a container of flowable medium, which may be provided in a powder form that may be hydrated with a pharmaceutically acceptable fluid (e.g., water, serum, or saline) prior to use, or in a ready to use form (e.g., a paste, putty, or slurry). The kit may further include instructions for use of the bone screw, device, or flowable medium to treat a bone defect (e.g., subarticular fracture, a defect of the spine or vetebra, or a defect of the radius, ulna, fibula, clavicle, humerus, pelvis, femur, patella, tibia, talus, calcaneus, navicular, cuneiforms, metatarsals, metacarpals, phalanges, scapula, ankle, teeth, or mandible).

In an embodiment of all aspects of the invention, the bone screw or device is sterilized after manufacture, prior to implantation, or prior to inclusion in a kit. In another embodiment of all aspects of the invention, the flowable medium is provided in a sterile form.

In another embodiment of all aspects of the invention, the bone screw includes a dual lead (e.g., two threads 180 degrees apart winding around the axis of the screw body), which provides for a faster advance of the screw in the bone. Alternatively, the bone screw can be designed as a dual lead, but have one thread omitted, which provides extra space between the thread for delivery channels.

In still another embodiment of all aspects of the invention, the bone screw includes a screw head, the circumference of which includes an internal edge break or chamfer on the inside of the radial hole just beyond the exterior of the screw head. The internal edge break or chamfer allows the flowable medium injected into the interior delivery channel (or cannula) of the bone screw to flow more easily through the delivery channel.

In other embodiments of all aspects of the invention, the width or diameter of the interior channel of the bone screw is substantially the same along the length of the bone screw. In other embodiments, the interior channel of the bone screw has more than one width or diameter (e.g., multiple different diameters) along the length of the bone screw. For example, the diameter of the interior channel may increase gradually along the length of the bone screw distal from the screw head or may decrease gradually along the length of the bone screw. In other embodiments, the interior channel of the bone screw may have several widths or diameters that alternate in size from large to small across several external delivery channels along the length of the bone screw.

In yet another embodiment of all aspects of the invention, the flowable medium may include a cohesiveness agent, an osteogenic agent, or a medicinal agent. The cohesiveness agent can be selected from the group consisting of: a) one or more polymers selected from polysaccharides, nucleic acids, carbohydrates, proteins, polypeptides, poly($\alpha$-hydroxy acids), poly(lactones), poly(amino acids), poly(anhydrides), poly(orthoesters), poly(anhydride-co-imides), poly(orthocarbonates), poly($\alpha$-hydroxy alkanoates), poly(dioxanones), poly(phosphoesters), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly($\varepsilon$-caprolactone), poly($\delta$-valerolactone), poly($\gamma$-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate) polyamide, and copolymers thereof; b) a homo- or copolymer having one or more monomers selected from the group consisting of acrolein potassium, (meth)acrylamides, (meth)acrylic acid and salts thereof, (meth)acrylates, acrylonitrile, ethylene, ethylene glycol, ethyleneimine, ethyleneoxide, styrene sulfonate, vinyl acetate, vinyl alcohol, vinyl chloride, and vinylpyrrolidone); c) a polyphenolic complexing agent selected from gallotannins, ellagitannins, taragallotannins, caffetannins, proanthocyanidins, catechin, epicatechin, chlorogenic acid, and arbutin; or d) an agent selected from alginic acid, arabic gum, guar gum, xantham gum, gelatin, chitin, chitosan, chitosan acetate, chitosan lactate, chondroitin sulfate. N,O-carboxymethyl chitosan, a dextran, fibrin glue, glycerol, hyaluronic acid, sodium hyaluronate, a cellulose, a glucosamine, a proteoglycan, a starch, lactic acid, a pluronic, sodium glycerophosphate, collagen, glycogen, a keratin, silk, and mixtures thereof. The osteogenic agent is selected from the group consisting of transforming growth factors-beta (TGF-$\beta$), activins, inhibins, and bone morphogenetic proteins (BMPs). The medicinal agent is selected from the group consisting of antibiotics, enzyme inhibitors, antihistamines, anti-inflammatory agents, muscle relaxants, anti-spasmodics, analgesics, prostaglandins, antidepressants, trophic factors, and hormones. In yet other embodiments of all aspects of the invention, the pharmaceutically acceptable fluid is selected from water, saline, a phosphate buffer, a biological fluid, in particular, blood or a fluid that includes blood components, and glycerol.

In other embodiments of all aspects of the invention, the pharmaceutical agent of the flowable medium may include, without limitation, an antibody, an antibiotic, a polynucleotide, a polypeptide, a protein (e.g., an osteogenic protein), an anti-cancer agent, a growth factor, a vaccine, and demineralized bone matrix. Osteogenic proteins include, without limitation, BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, and BMP-18. Anti-cancer agents include, without limitation, alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists, TNF alpha antagonists, endothelin A receptor antagonists, retinoic acid receptor agonists, immuno-modulators, hormonal agents, antihormonal agents, photodynamic agents, and tyrosine kinase inhibitors.

Definitions

As used herein, the term "about" means±10% of the recited value.

By "biocompatible" is meant that the material does not elicit a substantial detrimental response (e.g., an immune response) in the host. It should be appreciated that a foreign object introduced into a living body may induce an immune reaction that will have negative effects on the host. As used herein, the term "biocompatible" is intended to include those materials that may cause some inflammation but does not rise to the level of pathogenesis.

The term "bioresorbable" is meant the ability of a material to be resorbed by the body in vivo. The resorption process involves elimination of the original bioresorbable implant materials through the action of body fluids, enzymes, or cells. "Strongly bioresorbable" means that at least 80% of the total mass of material implanted in vivo is resorbed within one year.

By "bone defect" is meant any bone deficient region, such as a void, gap, recess, or other discontinuity in a bone. A bone defect can be artificially or naturally established, and can occur, for example, due to disease or trauma. Thus, a bone defect can occur as a consequence of pathologic or inflammatory diseases, formation and/or removal of a bone tumor, a surgical intervention, a congenital defect, or a bone fracture, and the like. For example, in the case of certain diseases, such as bone tumors, the bone defect may be artificially established due to removal of the tumor tissue. The bone screws of the invention can be applied, for example, in the repair of periodontal defects, in craniofacial or maxillofacial surgery or reconstruction, in hand surgery, in joint reconstruction, in fracture repair, in orthopedic surgical procedures, and in spinal fusion. The term "bony defect" is also intended to include anatomical sites where augmentation to a bony feature is desired by the patient in the absence of disease or trauma, such as in elective cosmetic surgery. Thus, the "defect" can be one that is subjectively perceived by the patient, and where augmentation of the bone deficient region is desired.

By "flowable medium" is meant, generally, a formulation of a resorbable or non-resorbable biocompatible agent, e.g., a polymer, such as a thermoset polymer or a thermoplastic polymer, e.g., PMMA (polymethylmethacrylate), a bone void filler material, a cement, or a pharmaceutical agent. In particular, the flowable medium may be a resorbable calcium phosphate or calcium sulphate cement, which may allow for the gradual replacement of the agent with bone.

Both resorbable and non-resorbable biocompatible agents, such as bone cements, have been used successfully in the treatment of bone defects.

Preferred calcium phosphate bone cements that can be used with the bone screws of the invention are described in, e.g., U.S. Pat. Nos. 5,783,217, 6,027,742, 6,214,368, 6,287,341, 6,331,312, 6,541,037, 6,953,594, 6,972,130, 7,150,879, 7,318,841, and 7,517,539, each of which is incorporated herein by reference.

By "bone fill material" or "infill material" is meant any material for infilling a bone that includes an in-situ hardenable material. The fill material also can include other "fillers," such as filaments, microspheres, powders, granular elements, flakes, chips, tubules and the like, autograft or allograft materials, as well as other chemicals, pharmacological agents, or other bioactive agents.

By "major diameter" of a bone screw is meant the diameter of the screw body, including its threads.

By "osteoplasty" is meant any procedure in which bone fill material and/or a flowable medium is delivered into the interior of a bone.

By "treating" or "treatment" is meant the medical management of a patient with the intent that an amelioration, repair, or prevention of an injury or disease, pathological condition, or disorder will result. This term includes active treatment, that is, treatment directed specifically toward improvement of the injury or disease, pathological condition, or disorder, and also includes causal treatment, that is, treatment directed toward removal of the cause of the injury or disease, pathological condition, or disorder. In addition, this term includes palliative treatment, that is, treatment designed for the relief of symptoms rather than the curing of the injury or disease, pathological condition, or disorder; preventive treatment, that is, treatment directed to prevention of the injury or disease, pathological condition, or disorder; and supportive treatment, that is, treatment employed to supplement another specific therapy directed toward the improvement of the injury or disease, pathological condition, or disorder.

"Vertebroplasty" includes its ordinary meaning and means any procedure wherein fill material is delivered into the interior of a vertebra.

Other features and advantages of the invention will be apparent from the following detailed description, and from the claims.

DETAILED DESCRIPTION OF THE INVENTION

Figure 1A:
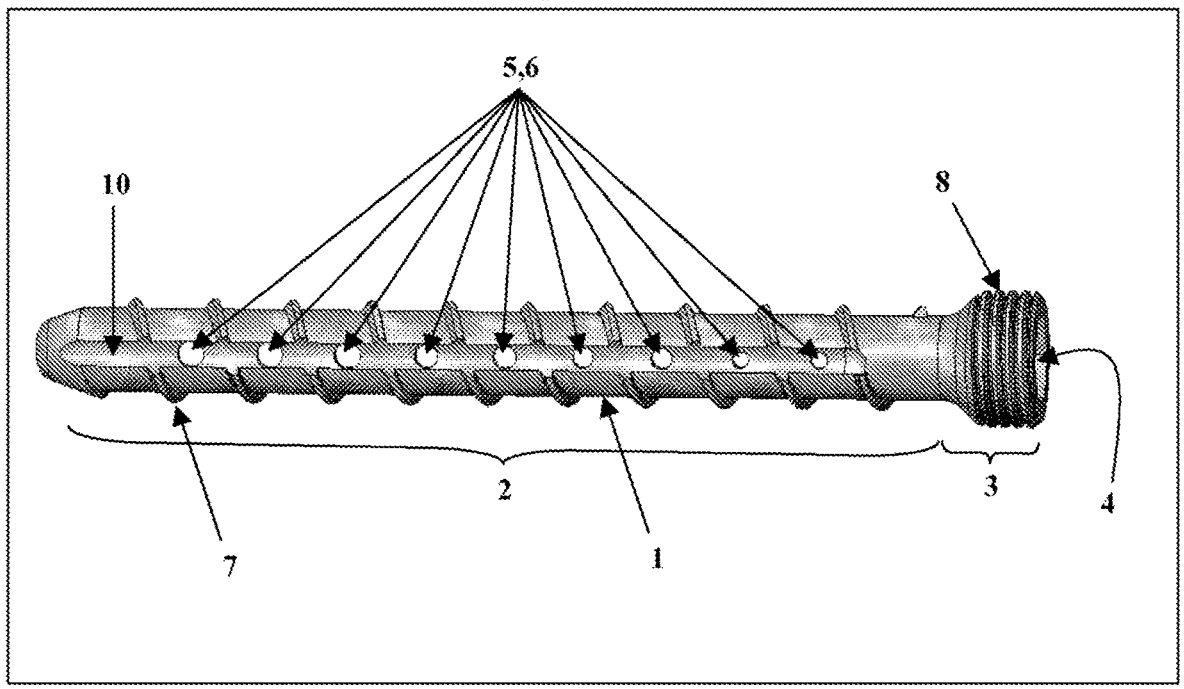
FIG. 1A is a side view of a schematic representation of an embodiment of a bone screw having straight exterior grooves.
Figure 1B:
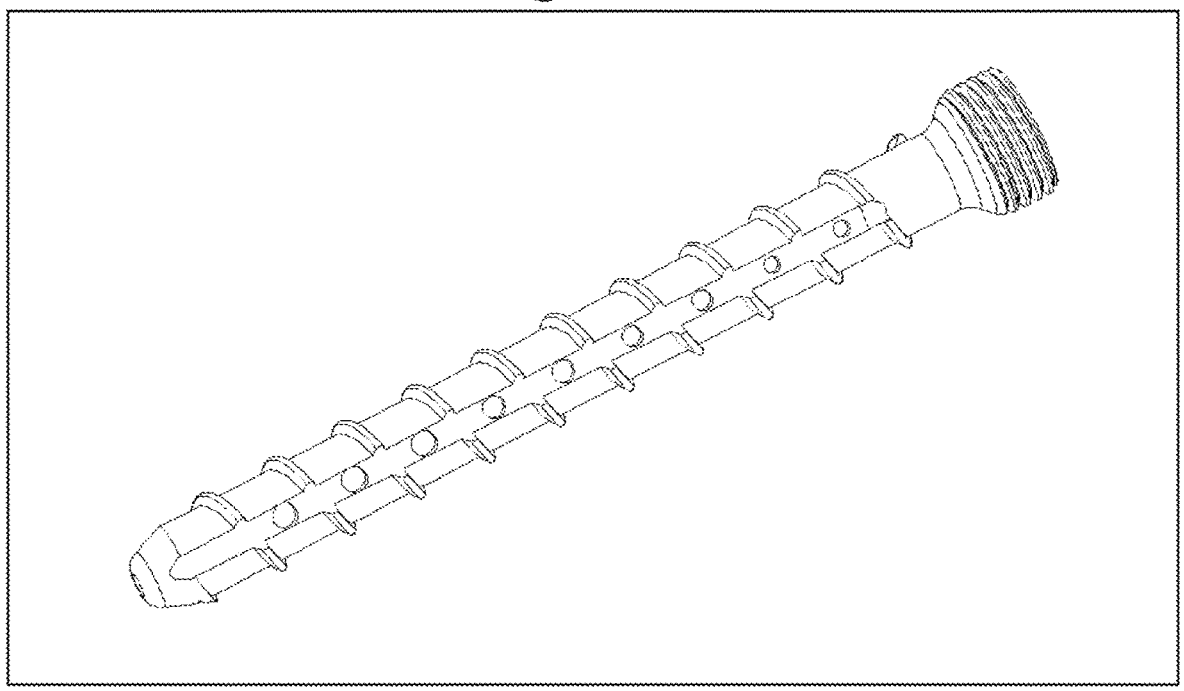
FIG. 1B is a diagonal view of the bone screw of FIG. 1A.
Figure 2A:
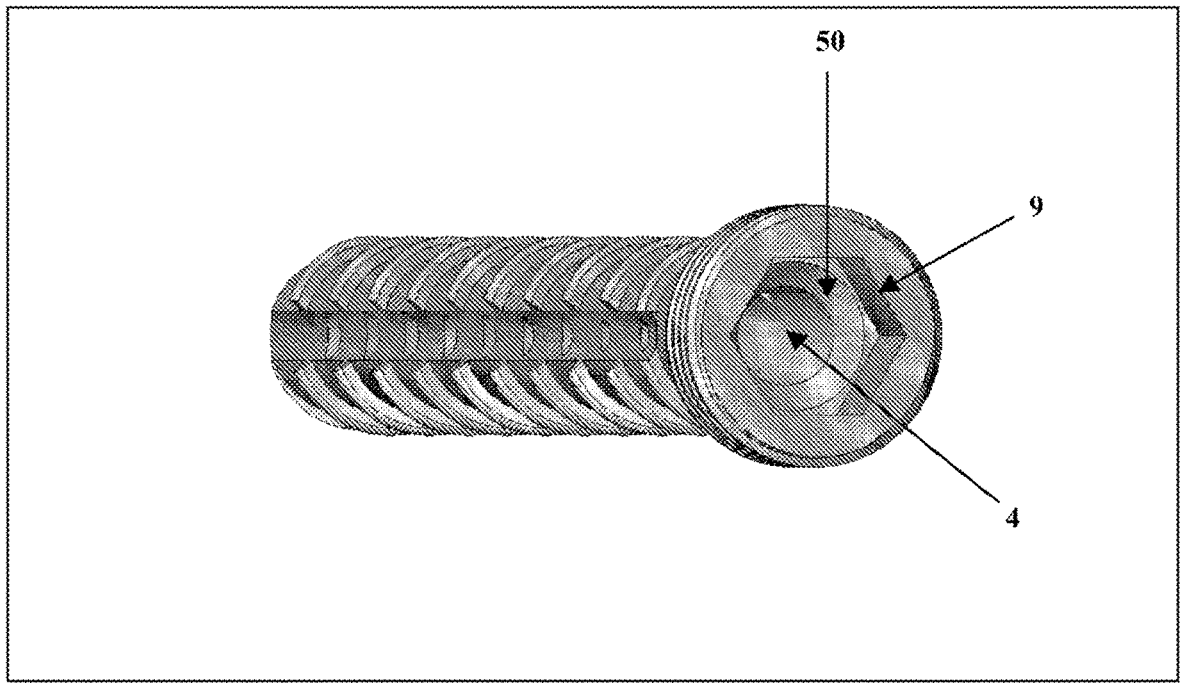
FIGS. 2A and 2B are schematic representations of the bone screw of FIG. 1A showing the interior channel and the top face of the screw head.
Figure 2B:
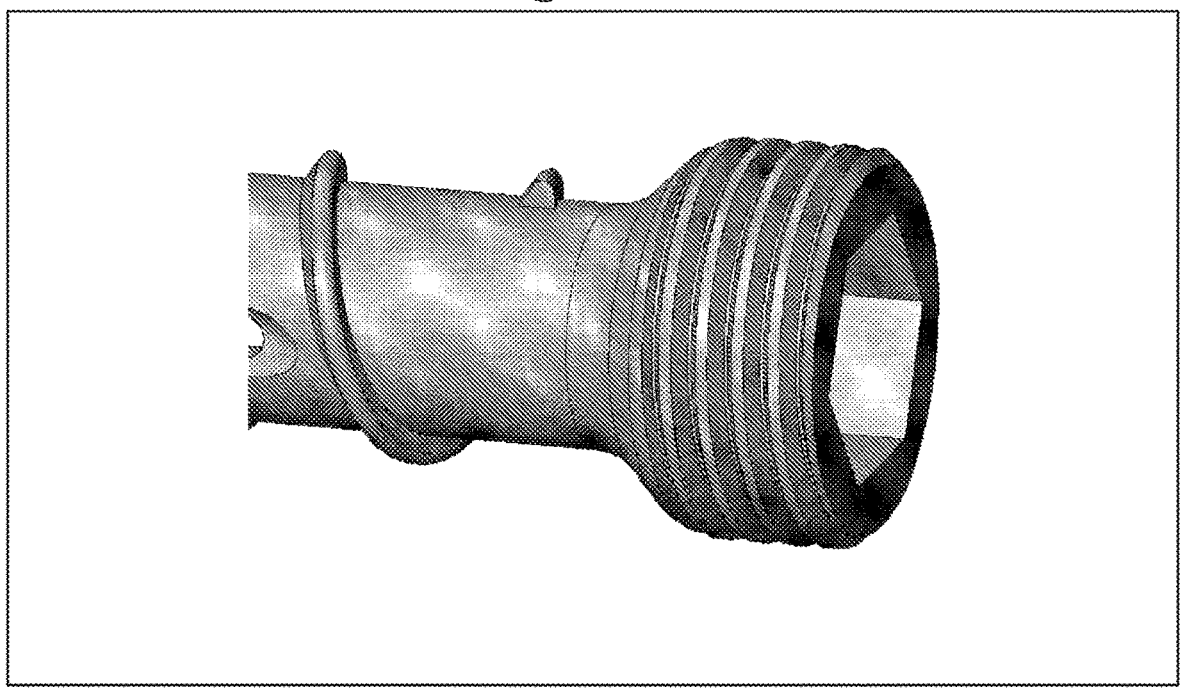

The invention features bone screws that allow the passage of a flowable medium (e.g., a bone cement, such as a resorbable calcium phosphate-based bone cement) through an interior channel of the screws and extrusion of the flowable medium through a plurality of delivery channels that lead to exterior openings along the body of the screws. Extrusion of the flowable medium to a position around the exterior of the bone screws promotes anchorage of the bone screws in bone after implantation and upon hardening of the flowable medium.

In some embodiments, the bone screws are designed to achieve a substantially uniform rate of flow of the flowable medium through substantially all (or at least a plurality of) the exterior openings along the body of the screws and to achieve a substantially uniform distribution of the flowable medium around the exterior surface of the bone screw, thereby anchoring it in the bone. A substantially uniform flow rate of a flowable medium through the exterior openings of the bone screw is achieved by, e.g., varying the cross-sectional area of each successive exterior opening distal to the screw head. In particular, the bone screw can be designed so that each successive exterior opening increases in cross-sectional area, such that extrusion of the flowable medium through each exterior opening is substantially the same.

The bone screws of the invention can be used even with bones of reduced quality (e.g., osteoporotic bone) or in revision surgeries (e.g., they can be used to replaced previously inserted bone screws).

The bone screws of the invention can be used, for example, in osteosynthesis to internally stabilize and/or join bones, e.g., fractured (broken) bones, either in conjunction with other mechanical devices, such as metal plates, pins, rods, or wires, or individually. Without limitation, bone screws include, e.g., small fragment screws, cortex screws, cancellous screws, dynamic hip screws, lag screws, non-self-tapping and self-tapping screws, and malleolar screws. The size and function of the bone screw of the invention may vary depending on its intended use (e.g., the bone screw may be fully threaded when used in the fixation of dense or cortical bone fractures and may be partially threaded when used in the fixation of cancellous bone to cortical bone). The head of the bone screw may be modified in order to operate with any of a number of appropriate drivers and drills known in the art.

The following description of the embodiments of bone screws of the invention and methods of use thereof are merely exemplary in nature and are in no way intended to limit the invention, its application, or uses. Moreover, while the present invention is described in detail with reference to several different bone screws of the invention, it will be appreciated by those skilled in the art that the present invention is not limited to the forms and materials specifically described, but may also be formed using related forms and other biocompatible materials, e.g., non-resorbable materials, such as titanium, and resorbable materials, such as allograft, ceramics, and ceramic-polymer mixtures.

There now follows a description of particular embodiments of the invention.

Structure

Referring to FIGS. 1A, 1B, 2A, and 2B, bone screw 1 includes threaded screw body 2 and screw head 3 attached to one end of screw body 2. Bone screw 1 further includes interior channel 4 extending longitudinally through screw head 3 and through screw body 2. In addition, bone screw 1 includes a plurality of radially-disposed delivery channels 5 connecting interior channel 4 to the exterior of screw body 2. Delivery channels 5 of bone screw 1 have exterior openings 6. The exterior openings 6 that are closest to screw head 3 have the smallest cross-sectional areas, while exterior openings 6 that are furthest from screw head 3 have the largest cross-sectional areas. This configuration achieves a substantially uniform flow rate of a flowable medium through delivery channels 5. The exterior openings 6 are positioned along the length and between threads 7 of screw body 2. Bone screw 1 may also include an optional interior edge break 50.

Screw head 3 is circular and includes screw head threads 8 on its exterior, to which a delivery manifold may be attached. Screw head 3 additionally contains hexagonal opening 9 internal to screw head 3, in which a rotational driver may be inserted. Screw body 2 additionally contains three straight exterior grooves 10 substantially equally spaced around screw body 2 and connecting exterior openings 6. In embodiments, bone screw 1 may have one or two external grooves 10 or may have more than three external grooves 10; the external grooves may be straight, helical, or a combination of the two.

Figure 3A:
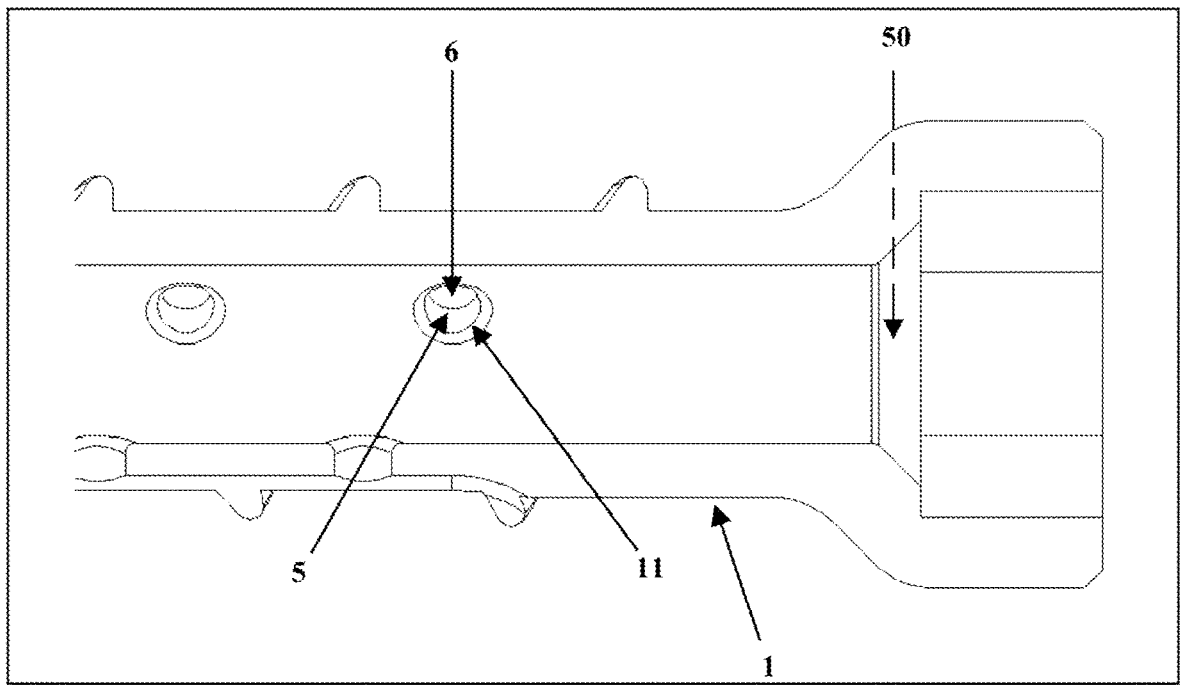
FIGS. 3A and 3B are sectional views showing the interior of the bone screw and the tapered delivery channels for enhanced flow.
Figure 3B:
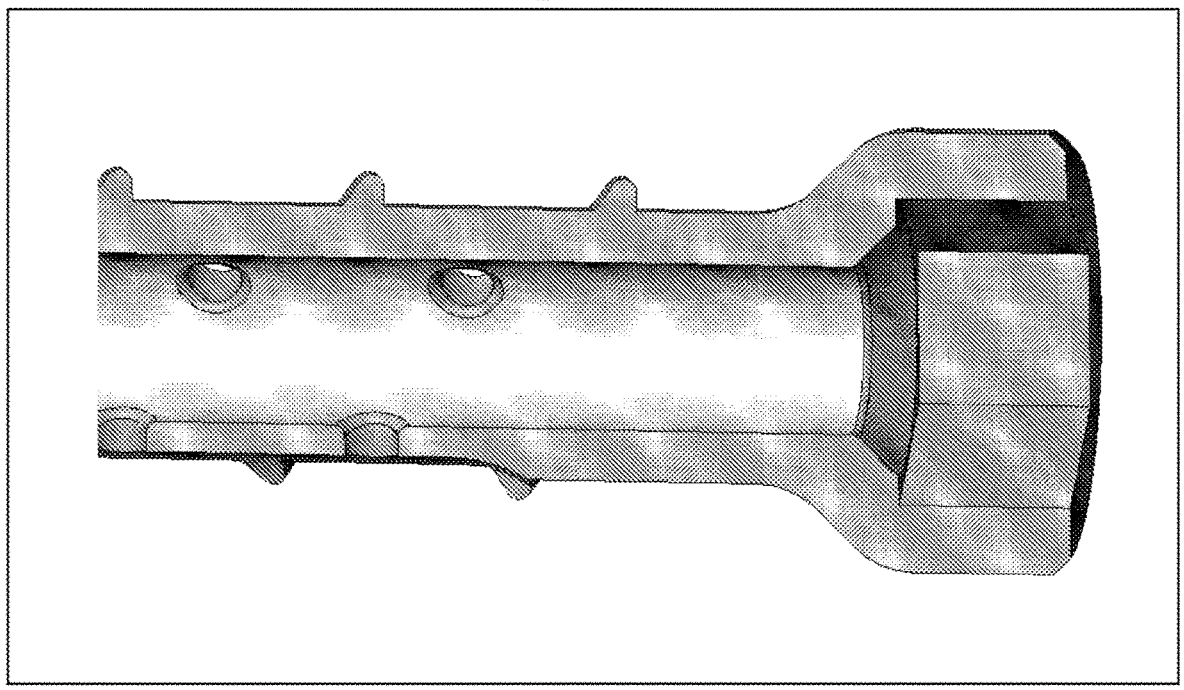
Figure 4A:
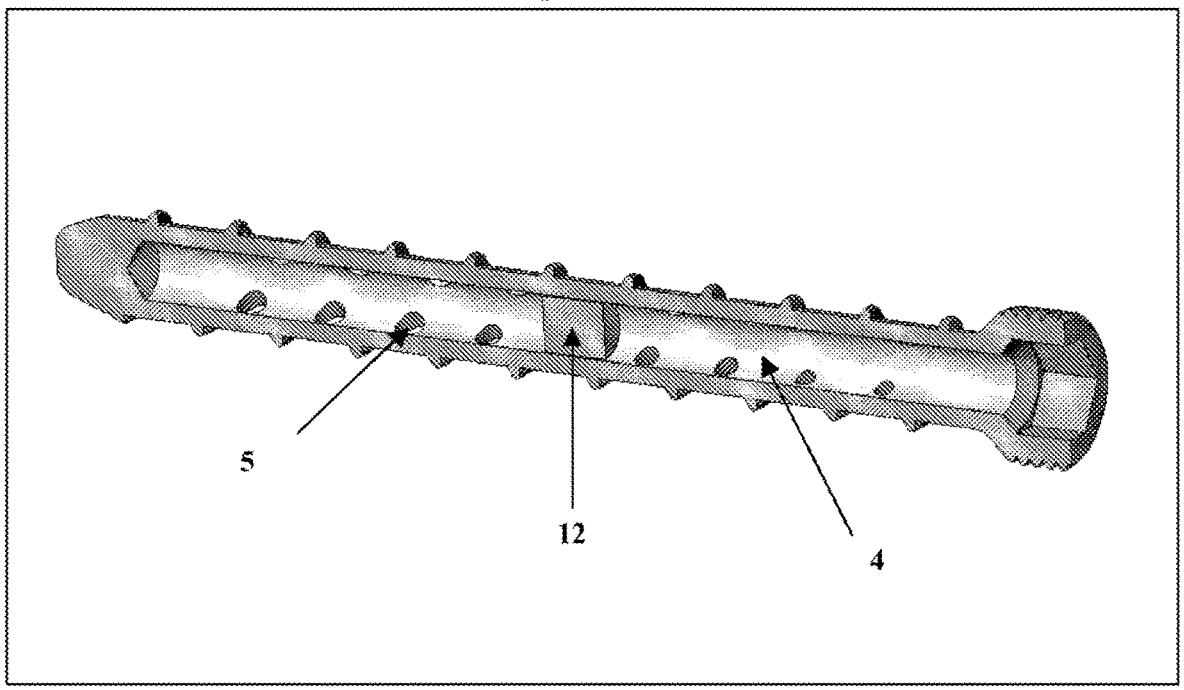
FIGS. 4A-4C are sectional views showing an internal plug that fully or partially occludes a portion of the interior channel of the bone screw.
Figure 4B:
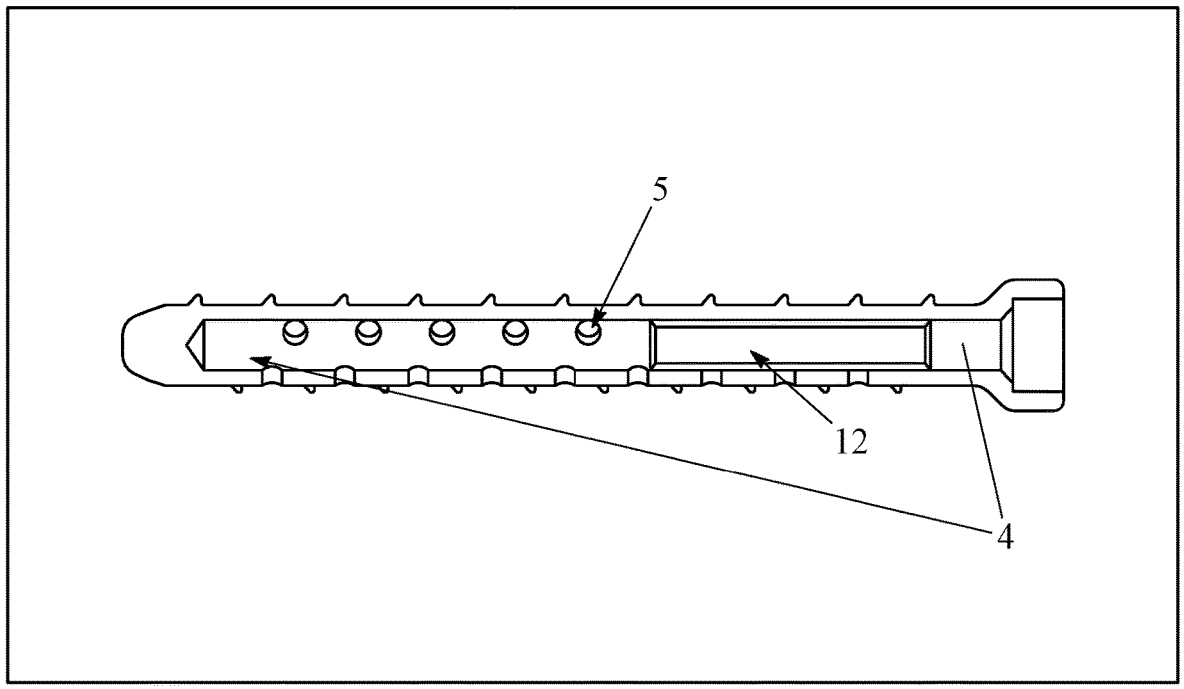
Figure 4C:
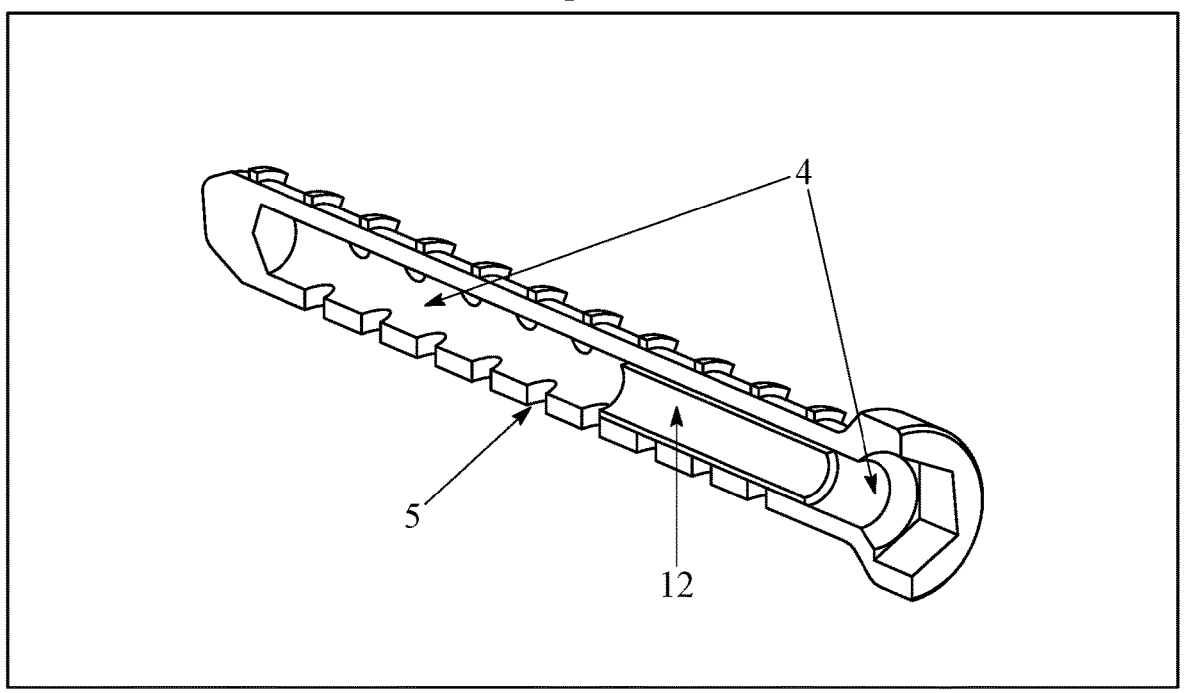
Figure 4D:
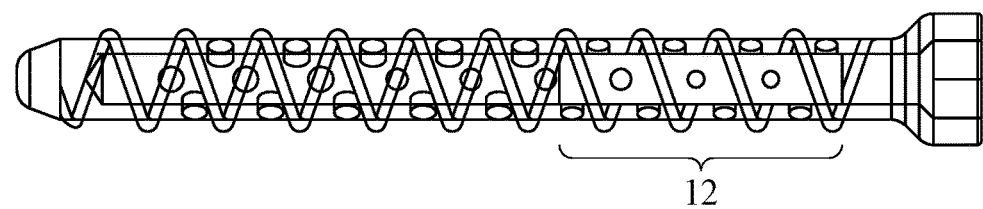
FIG. 4D is a side view of a bone screw showing an internal plug inside the interior channel of the bone screw.
Figure 4E:
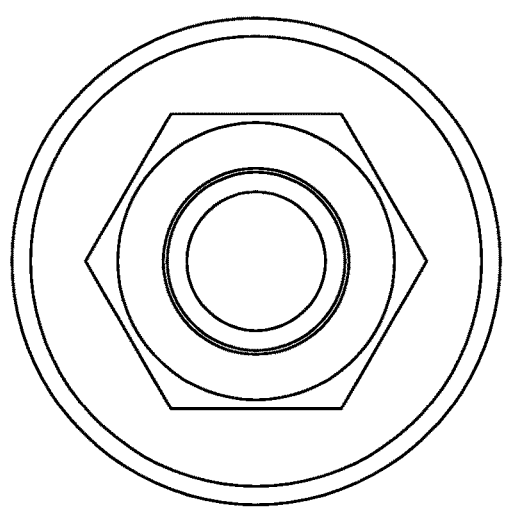
FIG. 4E is a top view of the bone screw of FIG. 4D.

Referring to FIGS. 3A and 3B, a portion of each delivery channel 5 is substantially cylindrical (although delivery channel 5 can have other shapes, such as a square shape, hexagon shape, diamond shape, etc.), while portion 11 closest to interior channel 4 may be tapered to enhance the flow characteristics of a flowable medium through delivery channel 5. Optional interior edge break 50 is also shown in FIG. 3A.

Referring to FIGS. 4A-4E, internal plug 12 is placed inside interior channel 4. Internal plug 12 may fully or partially block passage of a flowable medium distal to internal plug 12 in the direction heading away from screw head 3 as it moves through interior channel 4. Internal plug 12 may block a subset of delivery channels 5 and may be affixed within interior channel 4 or slidably disposed inside interior channel 4, thereby allowing for adjustment of its placement inside interior channel 4. Internal plug 12 may be solid, thereby preventing movement of flowable material beyond its position (FIG. 4A), or it may be substantially porous or hollow (FIGS. 4B and 4C), thereby allowing varying amounts of flowable material to flow through it to reach delivery channels 5 distal to the internal plug 12.

Figure 5A:
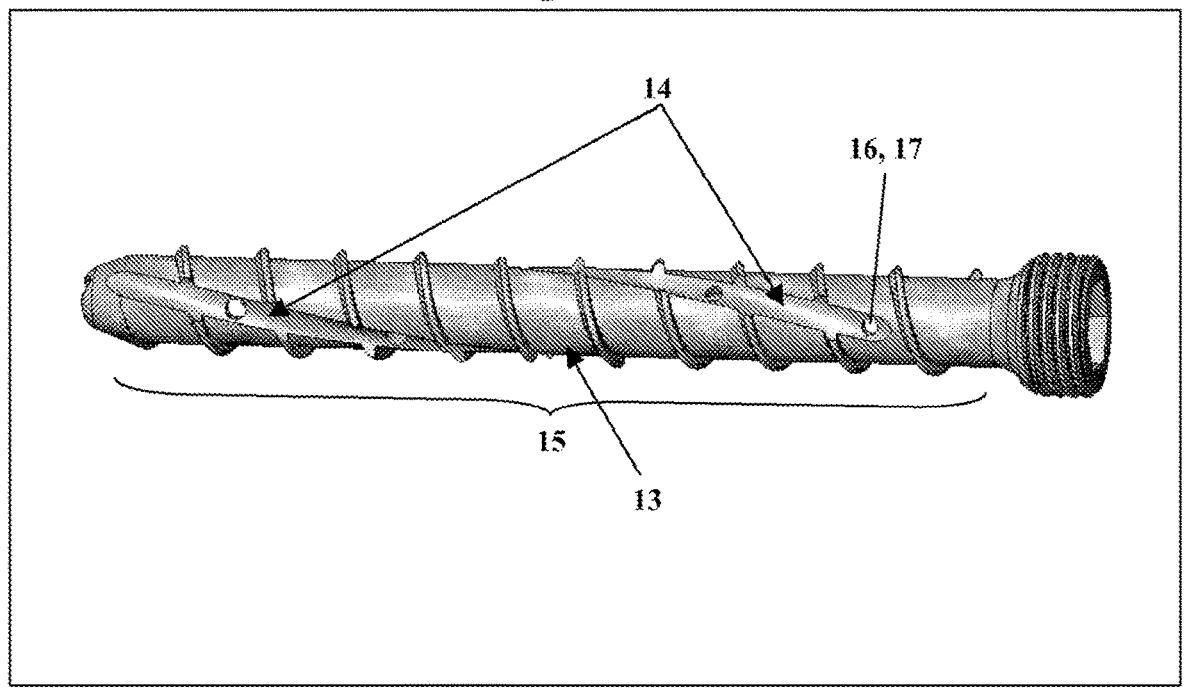
FIGS. 5A and 5B are side views of an embodiment of a bone screw having helical exterior grooves and delivery channels spaced opposite one another across the screw body.
Figure 5B:
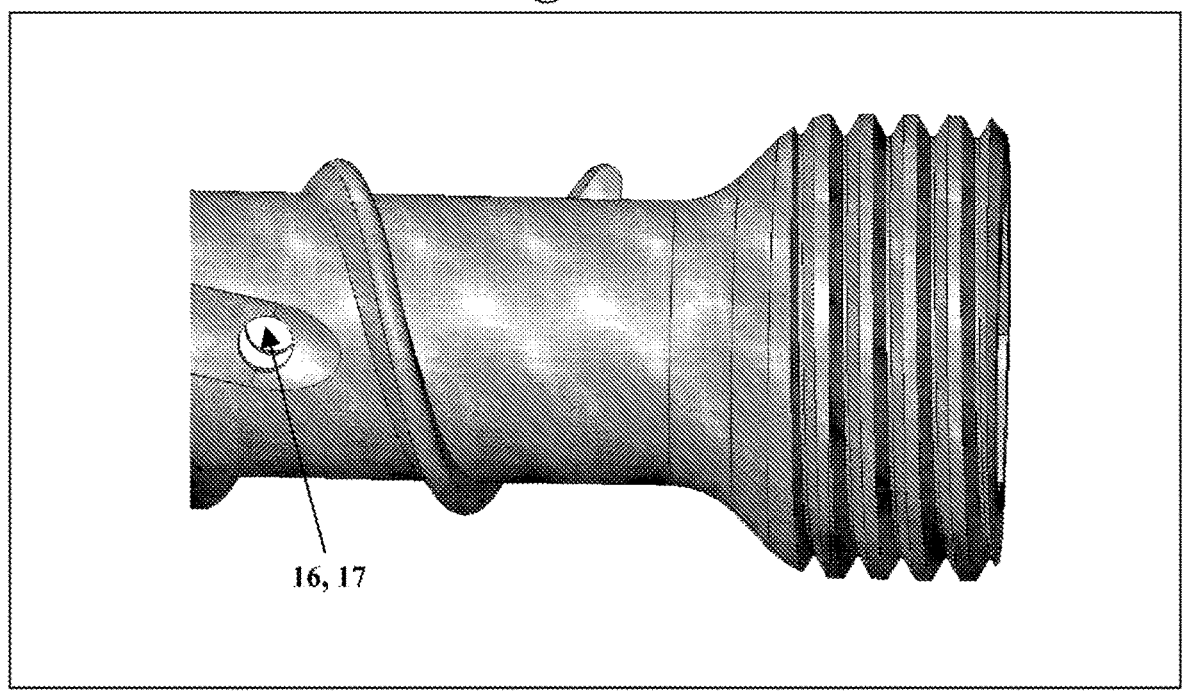

An alternative embodiment of a bone screw is shown in FIGS. 5A and 5B. Bone screw 13 of FIGS. 5A and 5B includes two helical exterior grooves 14 equally spaced around screw body 15. Each delivery channel 16 and exterior opening 17 is spaced directly opposite a second delivery channel 16 and exterior opening 17 across screw body 15.

Figure 6:
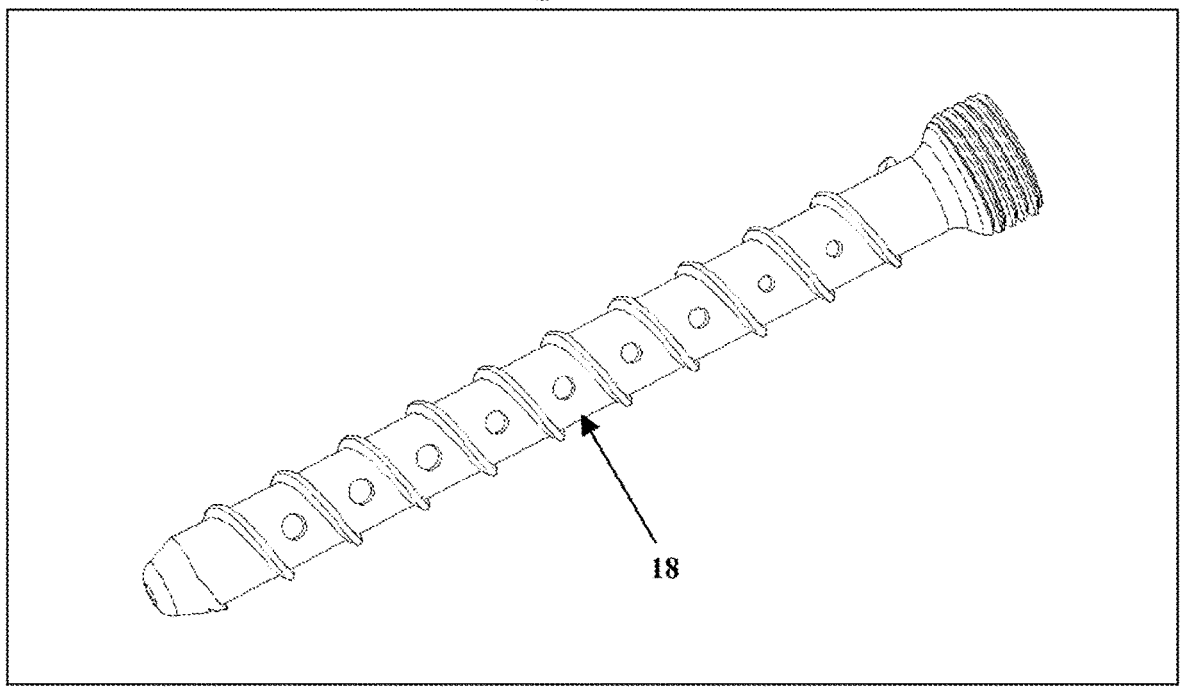
FIG. 6 is a diagonal view of an embodiment of a bone screw that lacks exterior grooves.

Referring to FIG. 6, bone screw 18 does not include exterior grooves.

Operation

Referring to FIGS. 7A and 8A-C, delivery manifold 19 in the form of, e.g., a Luer lock, is attached to to screw head 3 of bone screw 1, which has been positioned in proximity to a bone defect in the course of, e.g., a surgical procedure. Delivery manifold 19 includes threaded end 20 that is complementary to screw head threads 8 (as shown in FIG. 7B) of bone screw 1.

Figure 7A:
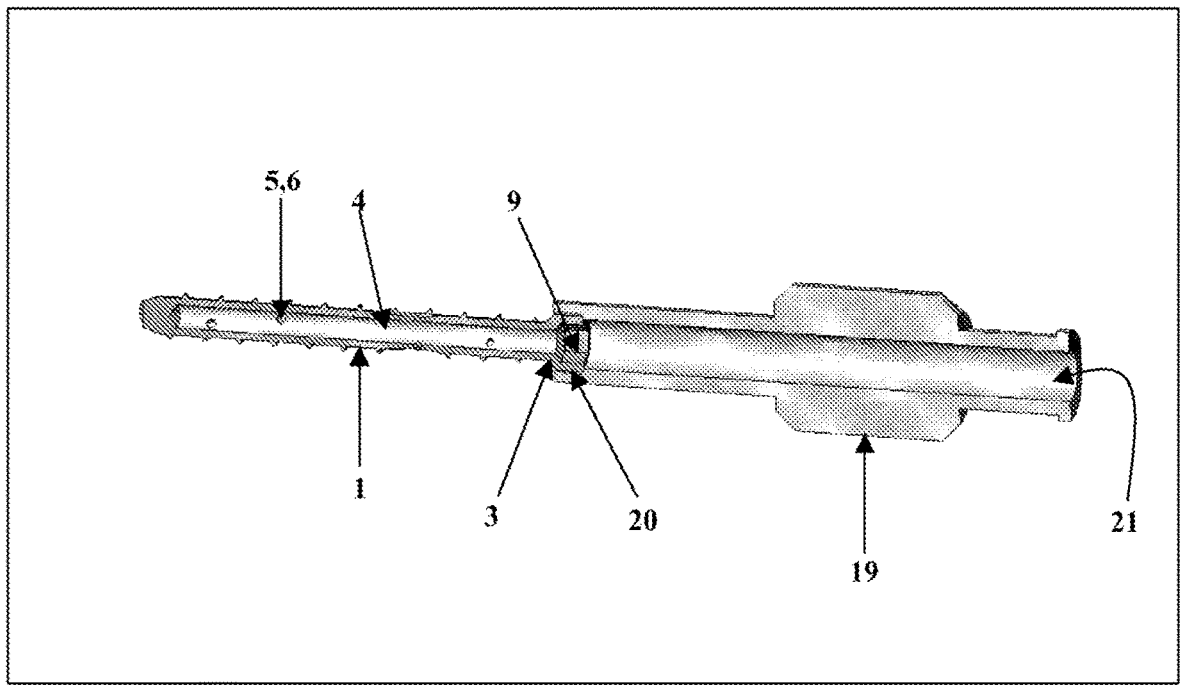
FIG. 7A is a sectional view of a device that includes a bone screw and a Luer lock delivery manifold coupled via complementary screw threads.
Figure 7B:
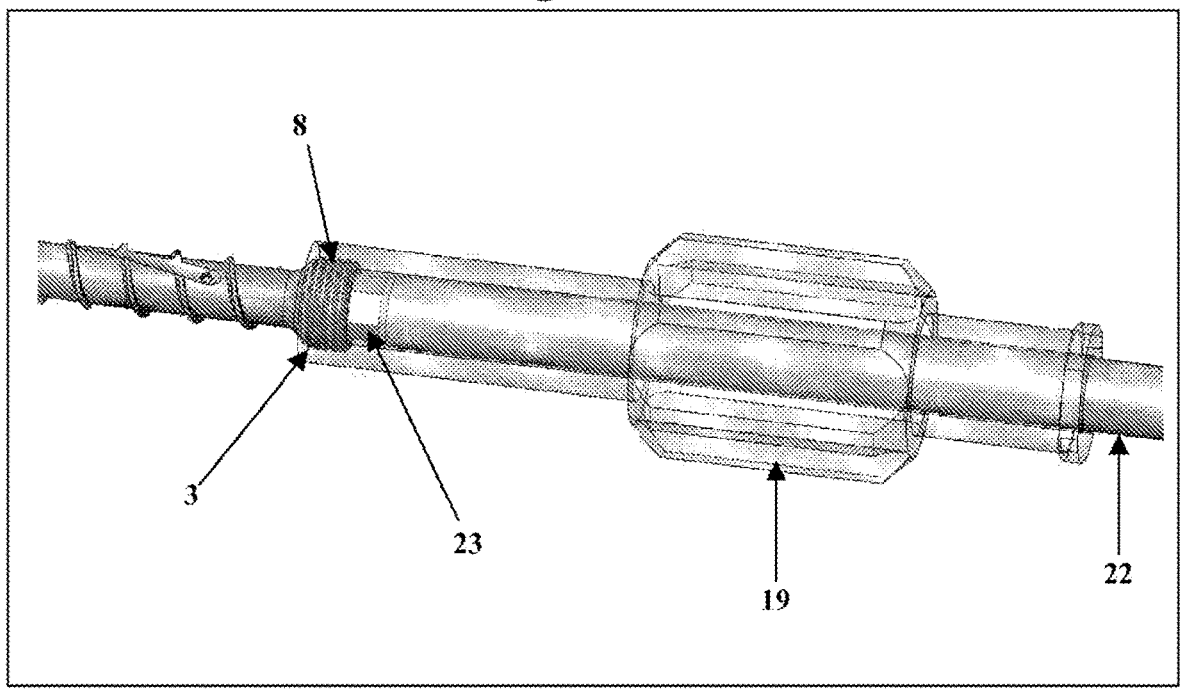
FIGS. 7B and 7C are side views of the device of FIG. 7A with a rotational driver inserted into the delivery manifold and engaging the screw head.
Figure 7C:
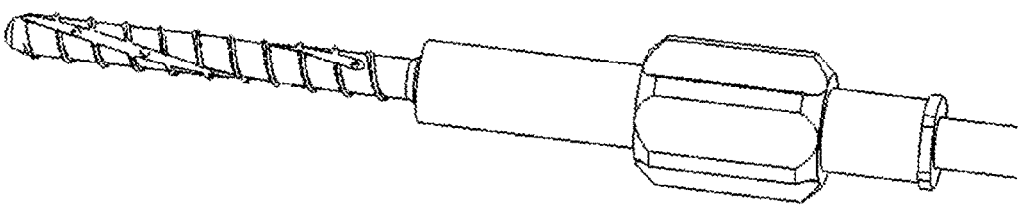
Figure 7D:
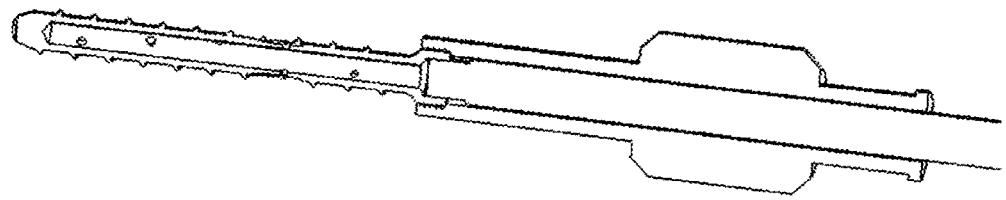
FIG. 7D is a sectional view of the device of FIGS. 7B and 7C.
Figure 7E:
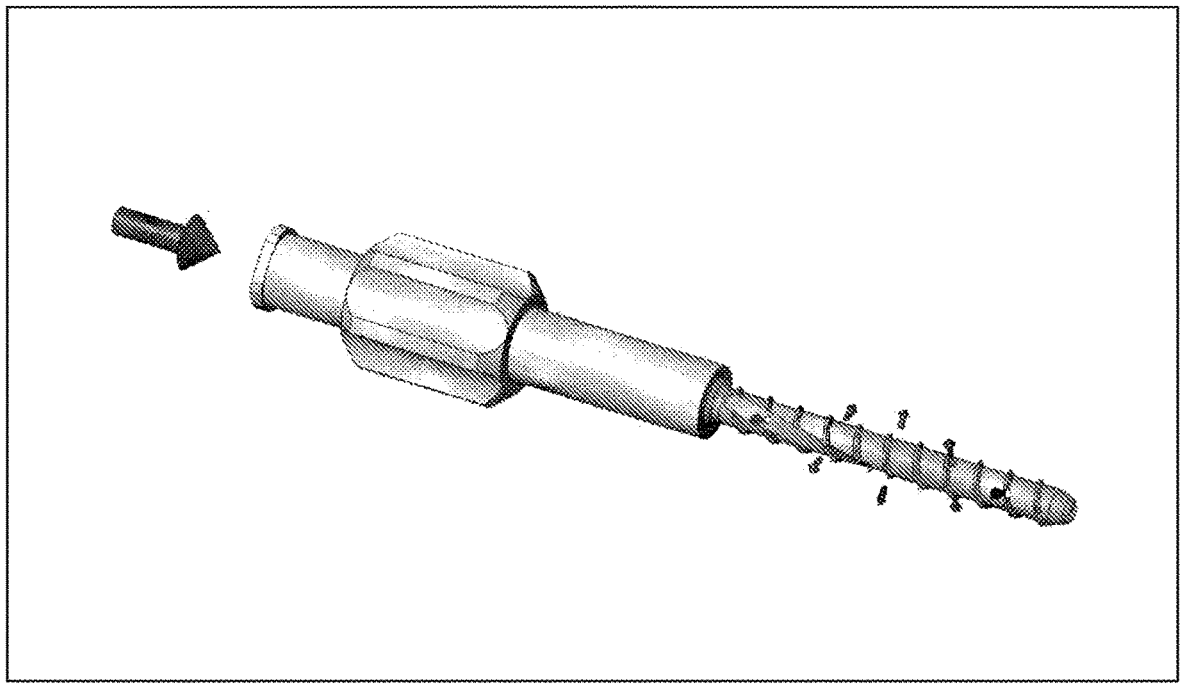
FIG. 7E is a side view of the device of FIG. 7A showing the flow path of flowable medium through the device.
Figure 7F:
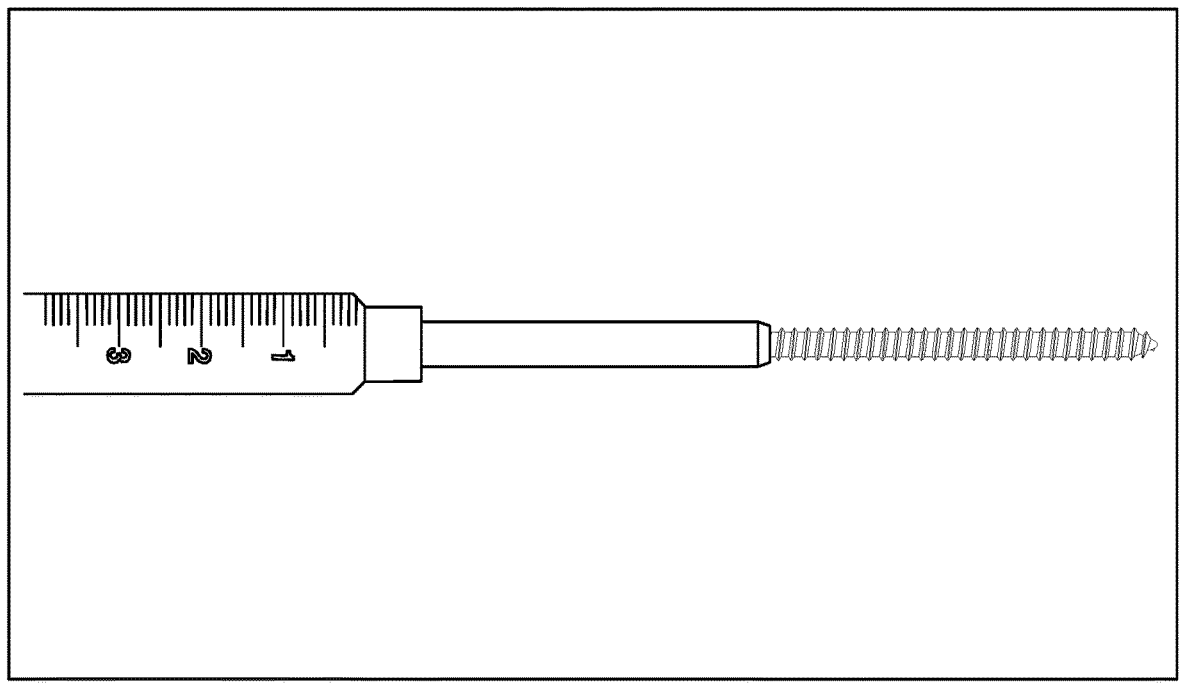
FIG. 7F is a side view of a device that includes a bone screw, a delivery manifold coupled to the bone screw via complementary screw threads on one end, and a syringe coupled to the delivery manifold on its other end.
Figure 8A:
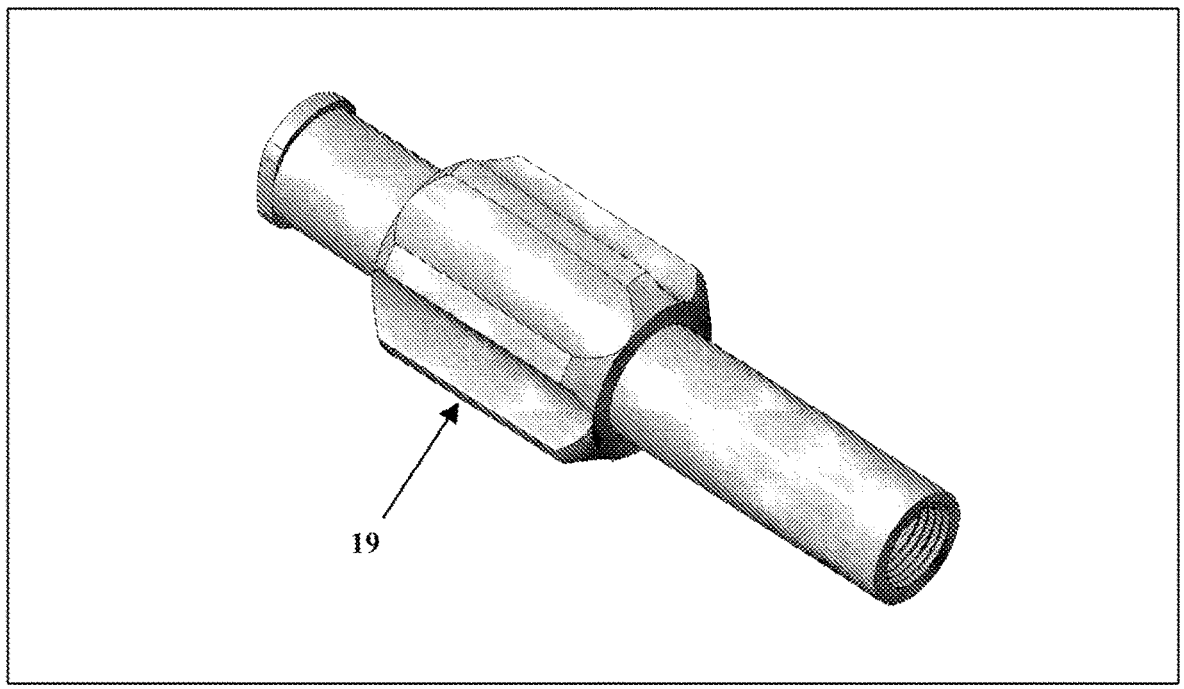
FIGS. 8A and 8B are diagonal views of a Luer lock delivery manifold.
Figure 8B:
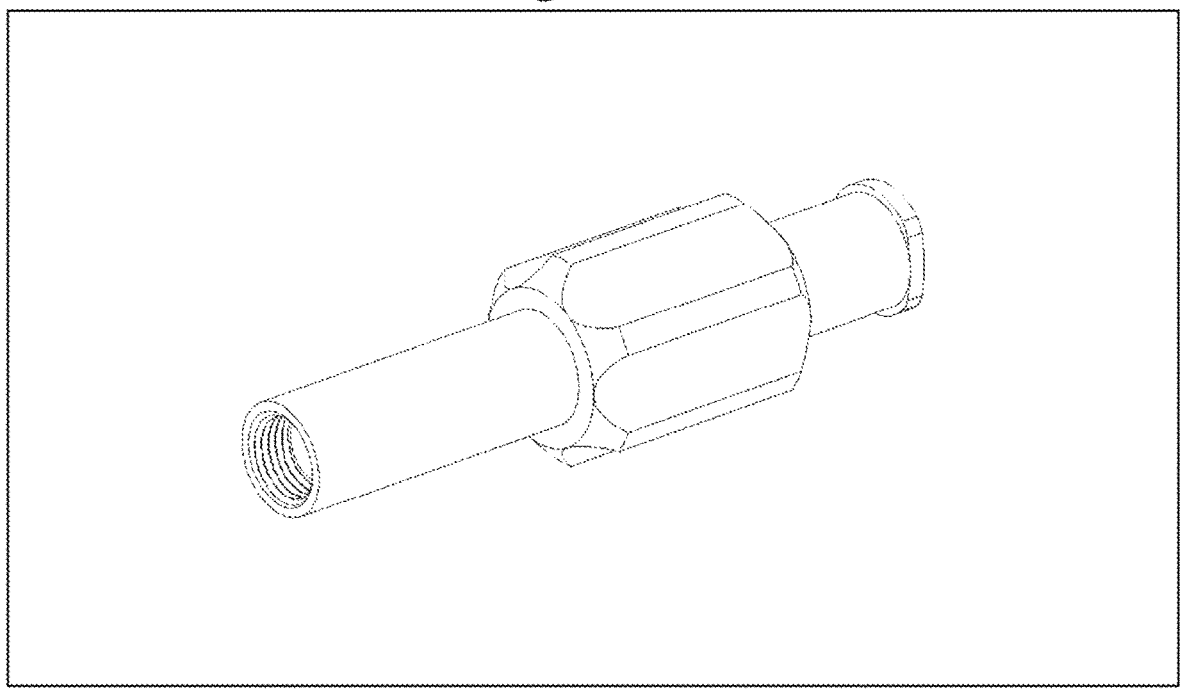
Figure 8C:
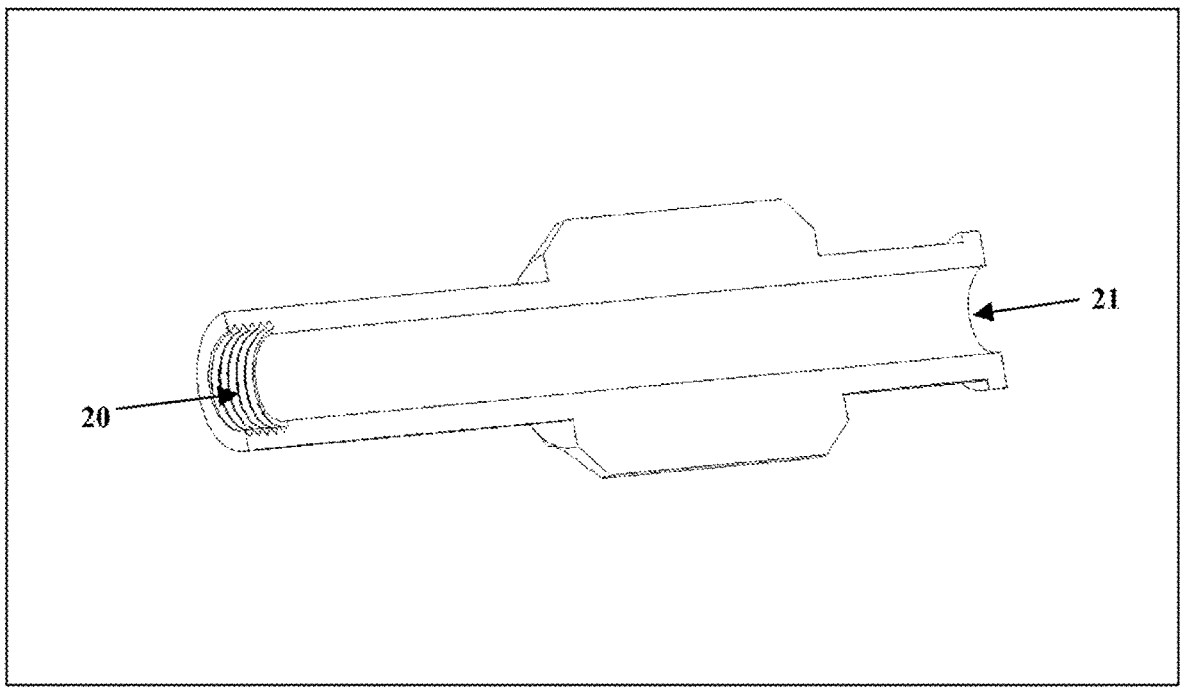
FIG. 8C is a sectional view of the Luer lock delivery manifold of FIGS. 8A and 8B.

Referring to FIGS. 7B-D, following attachment of delivery manifold 19, rotational driver 22 having, e.g., hexagonal end 23, as shown, or another driver shape, such as a Robertson driver, a slotted driver, a Phillips driver, a Torx driver, a triple square driver, a polydrive driver, a one-way clutch driver, a spline drive driver, a double hex driver, or a Bristol driver, is then inserted into delivery manifold 19, and hexagonal end 23 can engage hexagonal opening 9 (as shown in FIG. 7A) of screw head 3. Rotational driver 22 may be rotated clockwise or counterclockwise (depending upon thread direction) to tighten bone screw 1 into final or near-final position. Alternatively, bone screw 1 may be positioned into final or near-final position using a rotational driver in the absence of delivery manifold 19.

Rotational driver 22 is then removed and a flowable medium (e.g., a bone cement) may be introduced through proximal end 21 of delivery manifold 19 by, e.g., a syringe or other injection device. Alternatively, delivery manifold 19 may be removed from bone screw 1, filled with the flowable medium, and reattached to bone screw 1. The flowable medium may be introduced into bone screw 1 through delivery manifold 19 using, e.g., a syringe plunger moving through delivery manifold 19 in the direction from proximal end 21 to threaded end 20. The flowable medium is injected into bone screw 1 and its interior channel 4, and the cement is extruded substantially uniformly through delivery channels 5 and exterior openings 6. The flowable medium forms a substantially uniform coat around bone screw 1.

Following injection of the flowable medium, bone screw 1 is further tightened, if necessary, using rotational driver 22, which may be inserted through delivery manifold 19 or may be used after delivery manifold 19 is detached. After tightening of bone screw 1, delivery manifold, 19 is detached (if not already removed) and hexagonal opening 9 of screw head 3 may be sealed, e.g., using a sealable polymeric barrier, such as a silicone elastomer (e.g., Silastic®, Dow Corning Corporation. Midland, Mich.), or other means, such as a plug that may be secured by screwing onto the screw head.

Figure 9A:
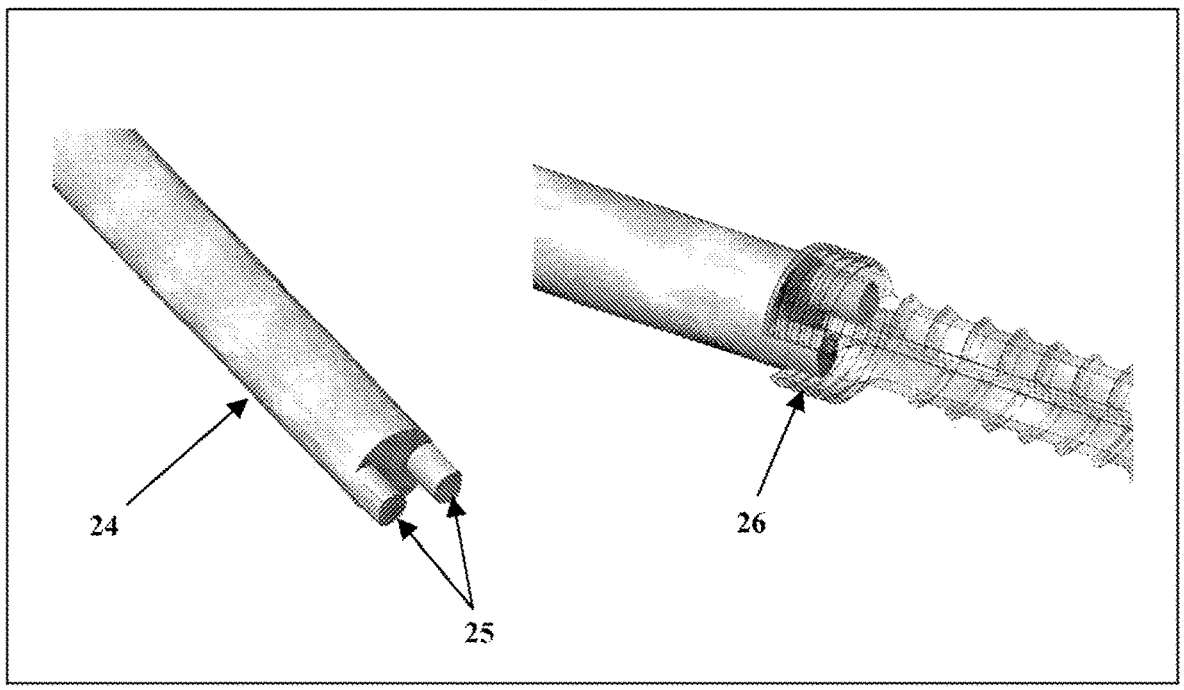
FIG. 9A is a diagonal view (left) of a spanner having two prongs and a diagonal view (right) of the spanner engaging a screw head with complementary holes.
Figure 9B:
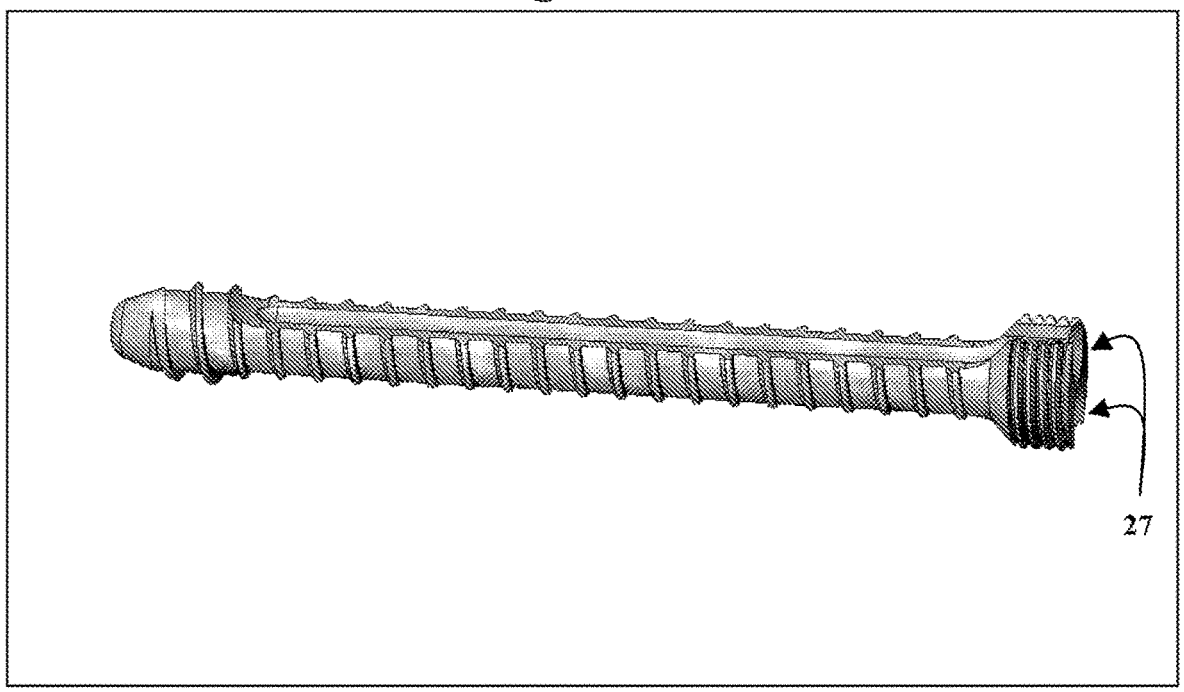
FIG. 9B is a side view of the bone screw shown in FIG. 9A.
Figure 9C:
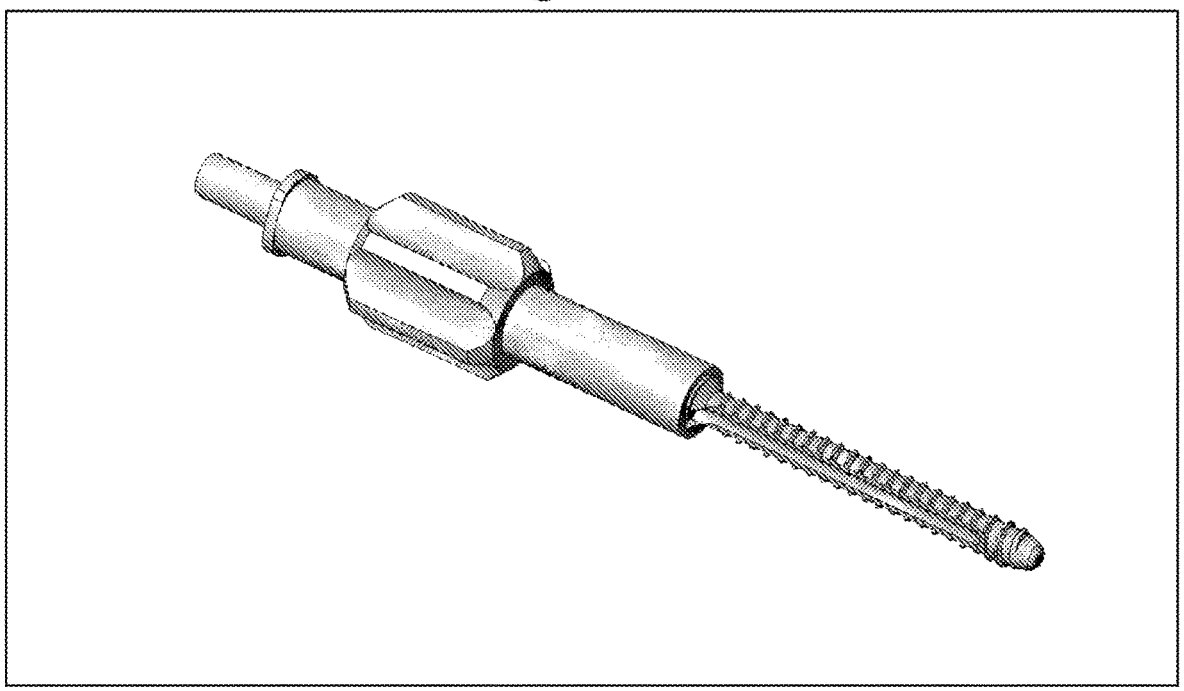
FIG. 9C is a diagonal view of a device that includes the bone screw of FIG. 9B and a Luer lock delivery manifold coupled via complementary screw threads, with the spanner of FIG. 9A inserted into the delivery manifold and engaging the screw head.
Figure 10A:
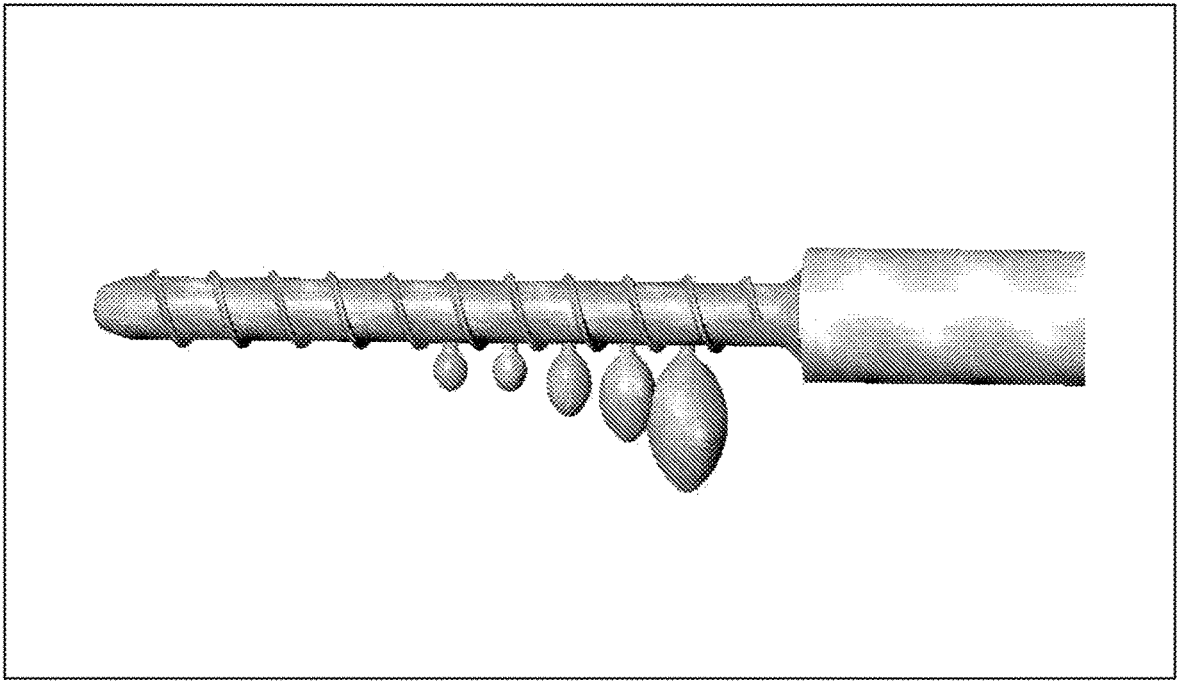
FIG. 10A is a side view of a bone screw having equal-sized exterior openings and an attached delivery manifold in which a flowable medium (e.g., a bone cement) has been injected. The flowable medium is shown being extruded through the delivery channels and exterior openings of the bone screw. The size of the bubble shown below each exterior opening indicates the volume of the flowable medium being extruded through the exterior opening.
Figure 10B:
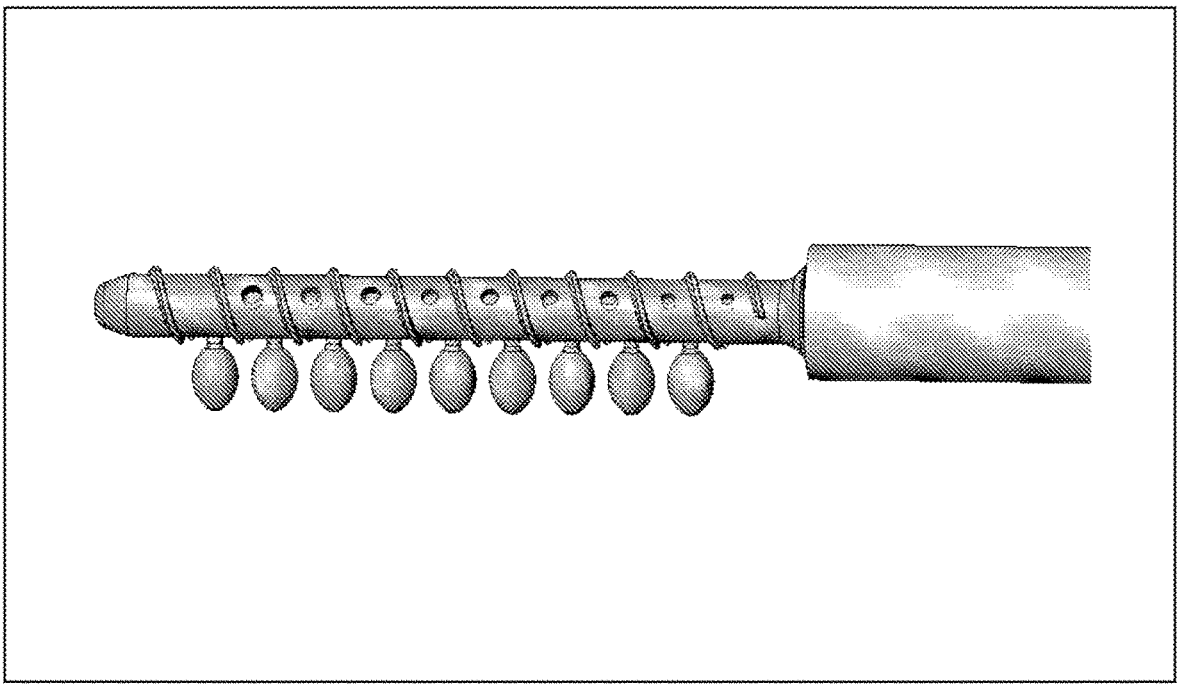
FIG. 10B is a side view of a device that is similar to that shown in FIG. 10A, but in which the bone screw contains exterior openings sized to achieve a substantially uniform flow rate through each exterior opening. The size of the bubble below each exterior opening indicates the volume of the flowable medium being extruded through the exterior opening.
Figure 11:
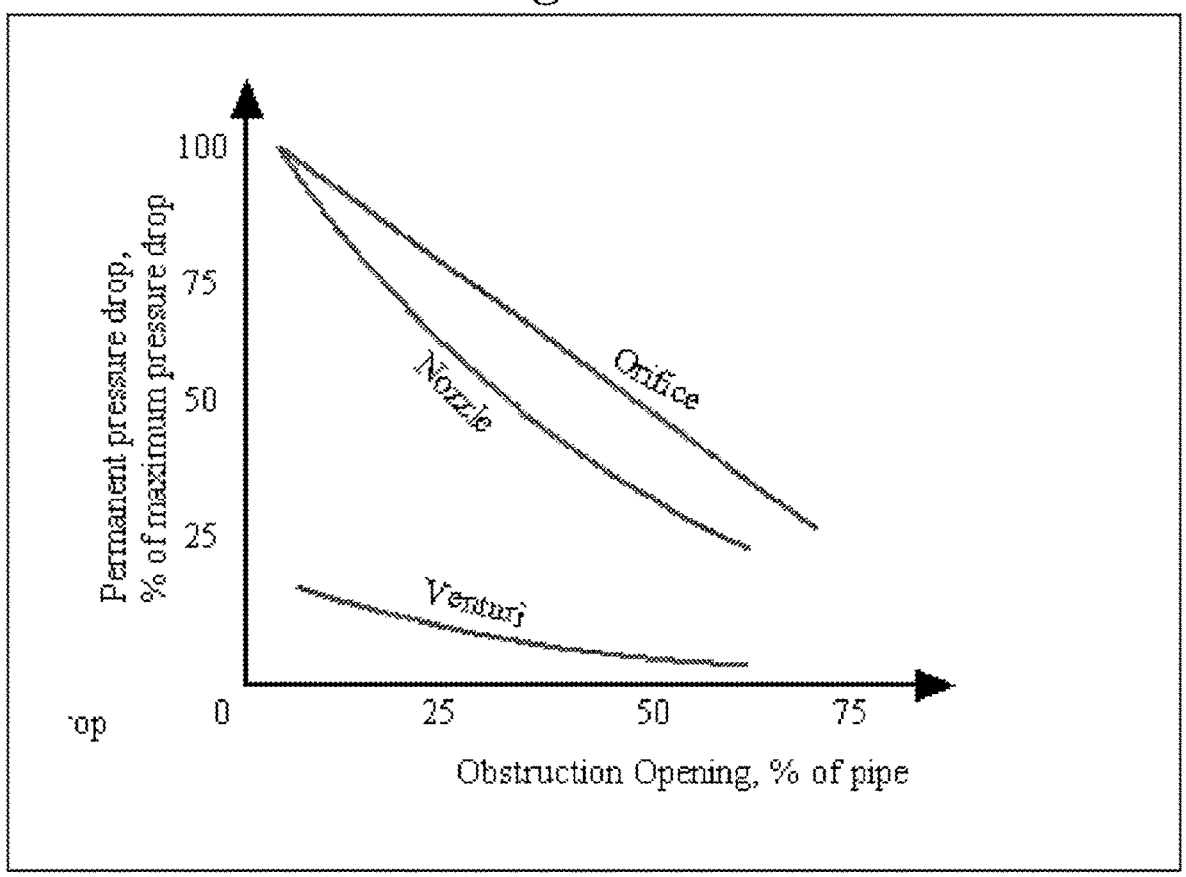
FIG. 11 is a graph showing the relationship of permanent pressure drop to size of obstruction opening in relation to non-cylindrical variations of delivery channel shape.
Figure 12A:
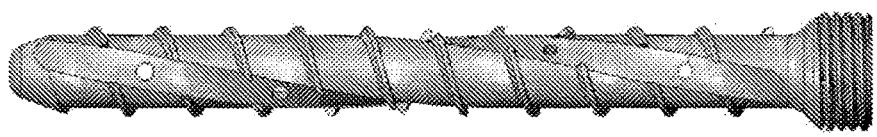
FIG. 12A is a side view of a metaphyseal bone screw having a major diameter of about 4.0 mm and a length of about 35 mm.
Figure 12B:
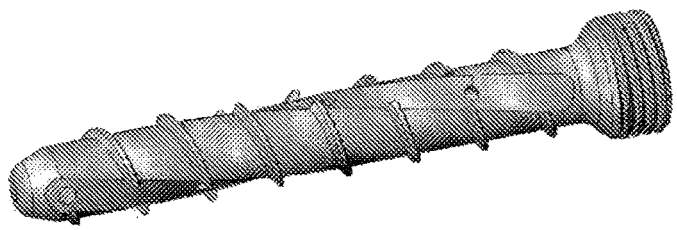
FIG. 12B is a side view of a metaphyseal bone screw having a major diameter of about 4.0 mm and a length of about 25 mm.
Figure 13A:
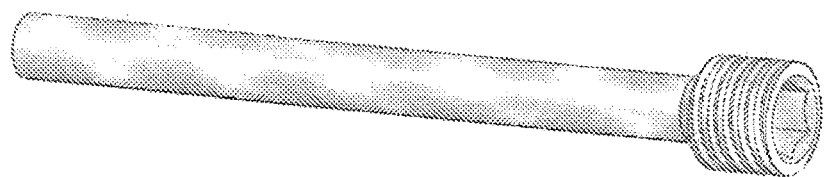
FIG. 13A is a side view of a screw-in plug that may be inserted into the interior channel of a bone screw.
Figure 13B:
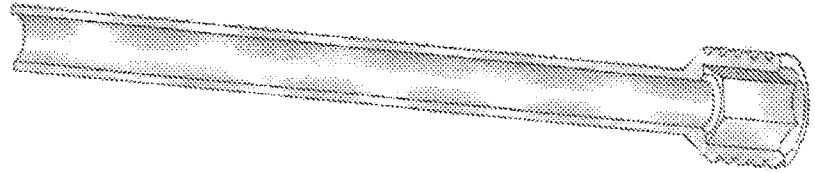
FIG. 13B is a sectional view of the screw-in plug of FIG. 13A.
Figure 13C:
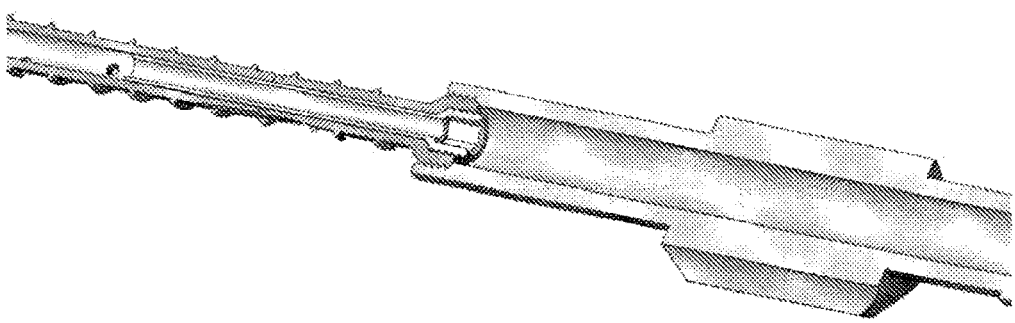
FIG. 13C is a sectional view of the device of FIG. 7A that includes the screw-in plug of FIG. 13A.
Figure 13D:
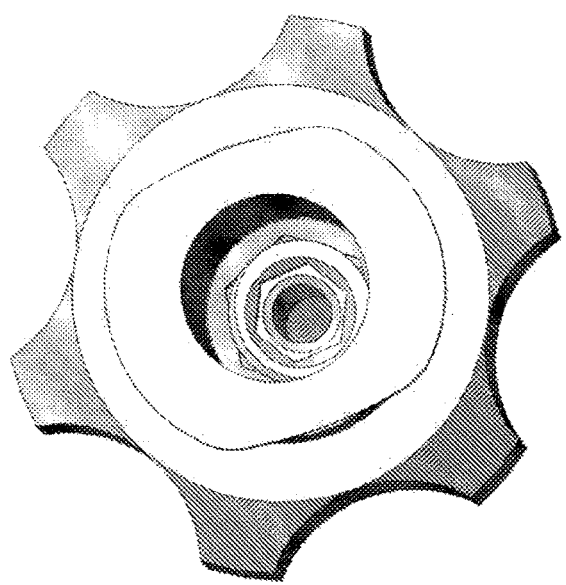
FIG. 13D is a top view of the device of FIG. 13C.
Figure 14A:
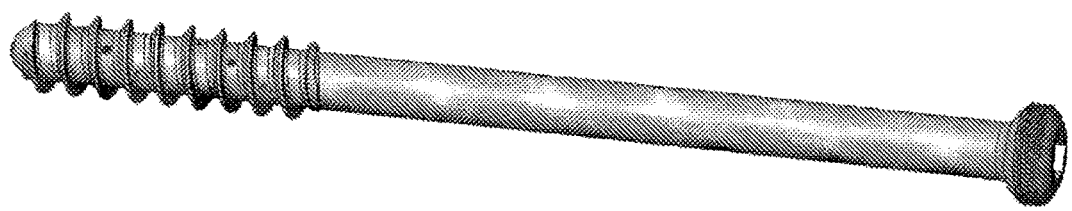
FIG. 14A is a side view of a bone screw that includes threads and delivery channels only in the portion of the screw body that is distal to the screw head. In an embodiment, the major diameter of the threaded portion of the bone screw can be 8.0 mm or less, e.g., 6.5 mm. The length of the threaded portion of the screw body can be, e.g., 15-30 mm, and the overall screw body length can be, e.g., 25-120 mm. The diameter of the interior channel is, e.g., 1.0-3.0 mm.
Figure 14B:
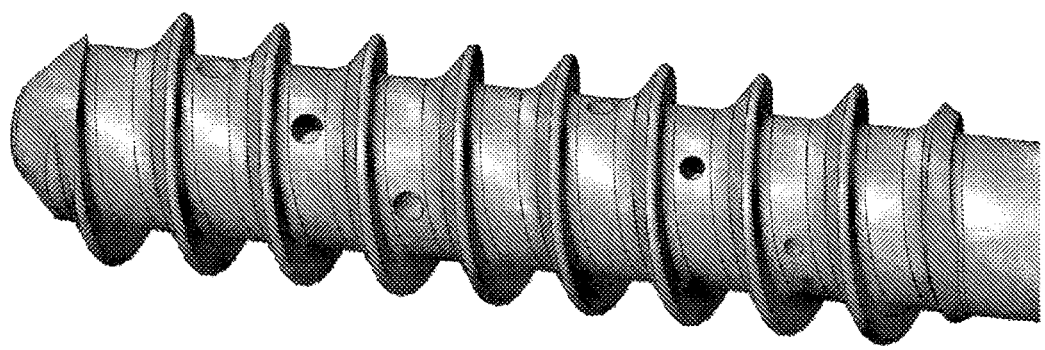
FIG. 14B is a close-up side view of the distal portion of the bone screw of FIG. 14A.
Figure 14C:
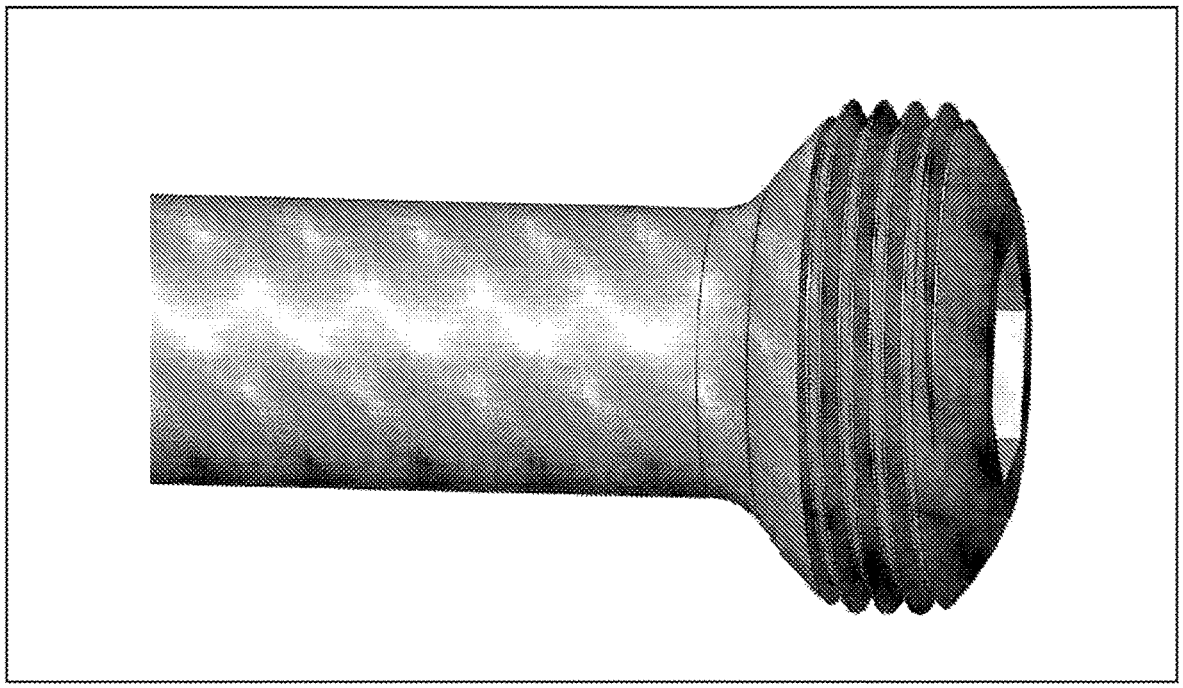
FIG. 14C is a close-up side view of the head of the bone screw of FIG. 14A.
Figure 14D:
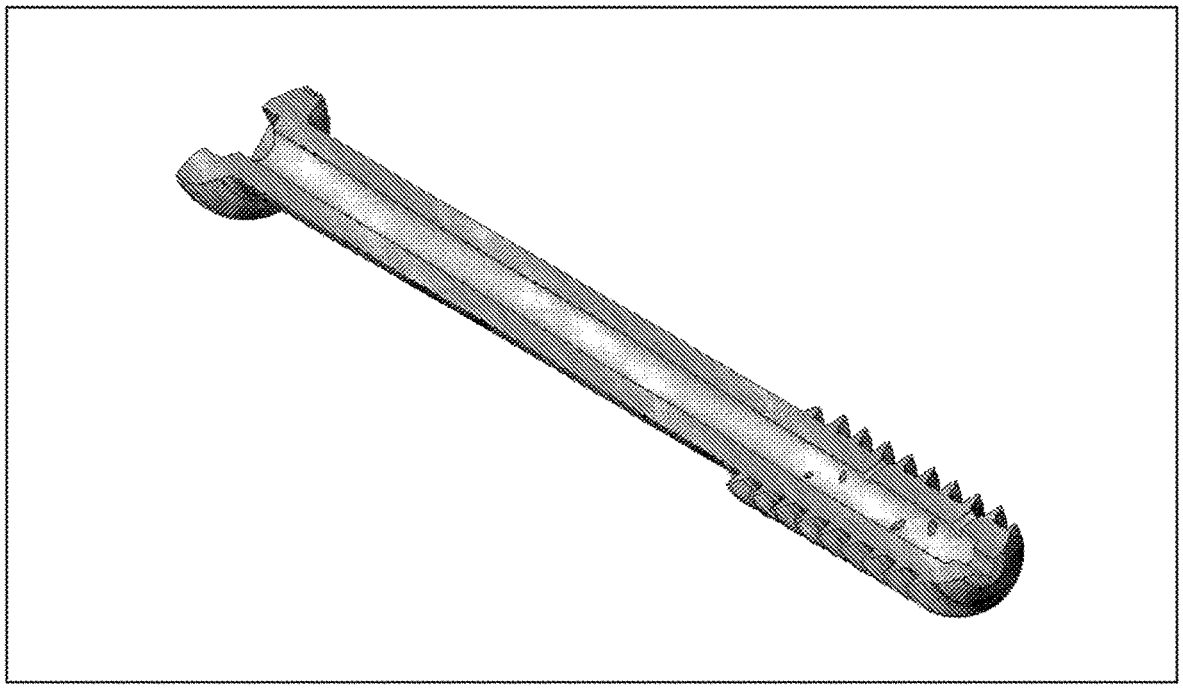
FIG. 14D is a sectional view of the bone screw of FIG. 14A.
Figure 15A:
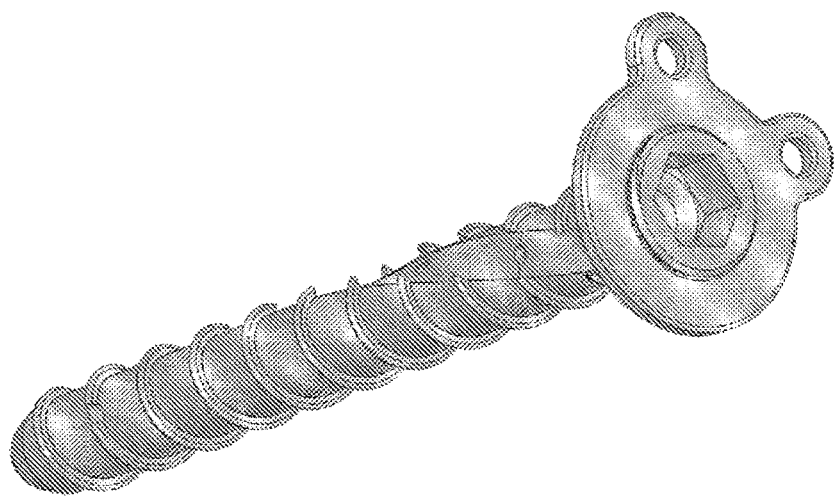
FIGS. 15A, 15B, 15C, and 15D are side views of a bone screw with alternative suture anchors affixed to the screw head.
Figure 15B:
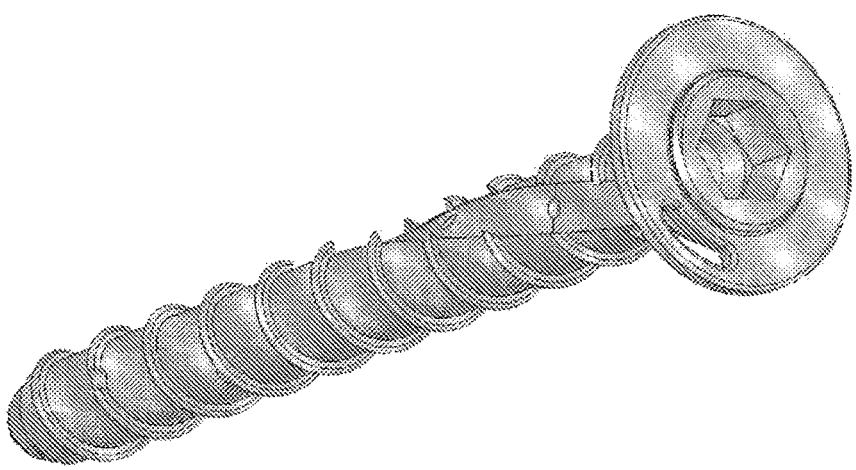
Figure 15C:
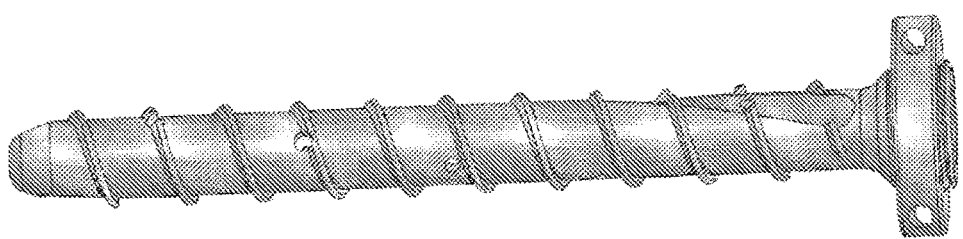
Figure 15D:
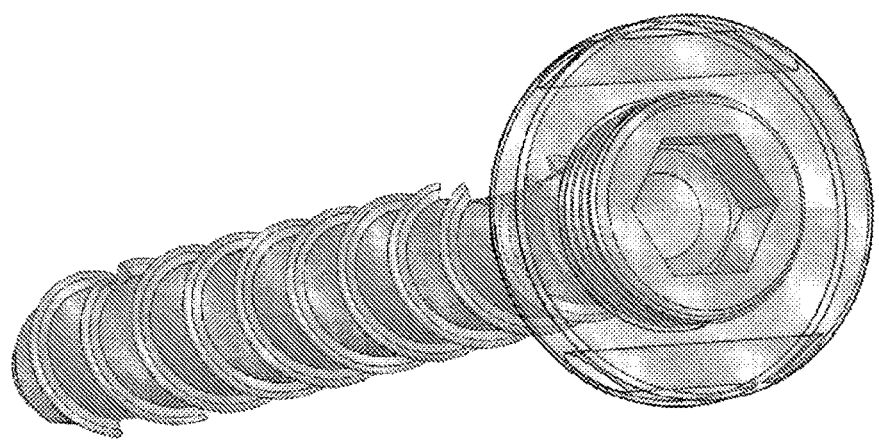

Referring to FIGS. 9A-9C, in an alternative embodiment, rotational driver 24 is a spanner having two prongs 25 (FIG. 9A), and screw head 26 includes complementary holes 27 (FIG. 9B) to engage rotational driver 24 (FIG. 9C).

The bone screws of the present invention provide numerous advantages over other bone screws known in the art. For example, in some embodiments of the bone screws of the present invention, the diameter of the interior channel is smaller than in cannulated bone screws in the art, resulting in improved strength and the option of reduced overall screw size. In addition, by having a smaller interior channel diameter, bone screws of the present invention are optimized for use with state-of-the-art bone cements, e.g., fourth-generation calcium phosphate-based bone cements, which have reduced viscosity and thus require application of less pressure than older bone cements. In additional embodiments, the threaded screw head allows for airtight attachment of a removable delivery manifold, e.g., a plastic manifold, which, in turn, facilitates loading of flowable medium by allowing a surgeon or other user to apply manual pressure rather than hydraulic pressure. This reduces the likelihood of unwanted introduction of air embolisms into the bone cavity or other surgical site. In addition, unlike prior art screws that require connection of a delivery manifold inside the rotational driver, producing very small orifices and correspondingly high operating pressure, bone screws of the present invention have no restriction in the flow path of the flowable medium, reducing the necessary operating pressure.

Furthermore, in some embodiments, e.g., screws designed for use in anterior cruciate ligament reconstruction, the diameter of the screw head is substantially the same as the diameter of the screw body, allowing for total implantation of the screw head within the bone, as the screw may be driven by a rotational driver inserted inside the screw head.

It is also significantly easier to remove, or adjust the position of, a bone screw of the present invention that has been placed in a surgical site, in comparison to bone screws of the art. Because the rotational driver is inserted inside the screw head, it is not necessary to grasp the external surface of the screw head in order to remove an implanted screw prior to hardening of the cement.

Upon hardening of the cement around a bone screw of the present invention, the bone screw is more stable and secure than a conventional screw because of the even distribution of cement that covers a large percentage of the surface area of the screw body and contacted bone. This increased stability reduces the likelihood of "backout" of a screw from the surgical site, which may occur with a conventional screw.

In additional embodiments, the presence of exterior grooves facilitates equalized distribution of flowable medium along the exterior surface of the screw. For example, if one exterior opening is blocked, flowable medium from an adjacent exterior opening may flow along an exterior groove to "back-fill" or compensate for the blocked opening. The presence of exterior grooves, in particular, straight exterior grooves, can also increase the strength characteristics of the screw body.

In additional embodiments, use of an adjustable interior plug allows for selective delivery of flowable medium to desired delivery channels while blocking off other delivery channels. Such a plug may be designed to be pushed in or screwed in and may be either permanent or removable. In addition, in some embodiments, the tip or distal end of the screw body, i.e., the end of the screw body distal to the screw head, may be manufactured to be open or closed; in open embodiments, a removable tip plug may be added as needed according to the surgical indication. The inclusion of such adjustable plugs significantly increases the flexibility of use of bone screws of the present invention.

EXAMPLES

The following examples are to illustrate the invention. They are not meant to limit the invention in any way.

Example 1: Use of a Bone Screw of the Invention to Repair a Fracture or Other Bone Defect A bone screw of the invention can be used to provide fracture support, e.g., for a subarticular fracture, in conjunction with conventional fixation. The site to be supported can be accessed using either a percutaneous or open technique. The extraction technique preferably ensures maximal bone conservation.

Uni-Cortical and Bi-Cortical Fixation

Figure 18A:
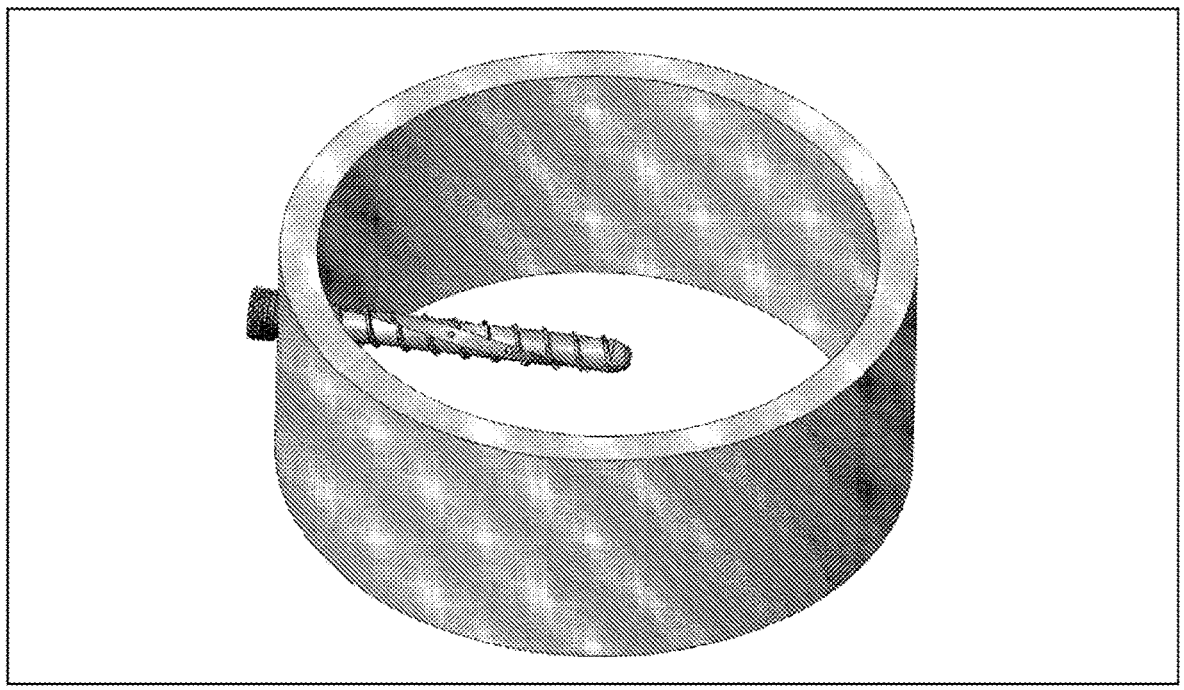
FIG. 18A is a side view of a unicortical insertion of a bone screw into a simulated cross-section of bone.

A bone screw of the invention can be used for uni-cortical fixation to cross one of the sections of the thick cortical wall of a bone, as shown schematically in FIG. 18A. An exemplary bone screw for uni-cortical fixation is, e.g., 25-55 mm long, with, e.g., a 4.0 mm major diameter and, e.g., a 1.6 mm interior channel diameter.

Figure 18B:
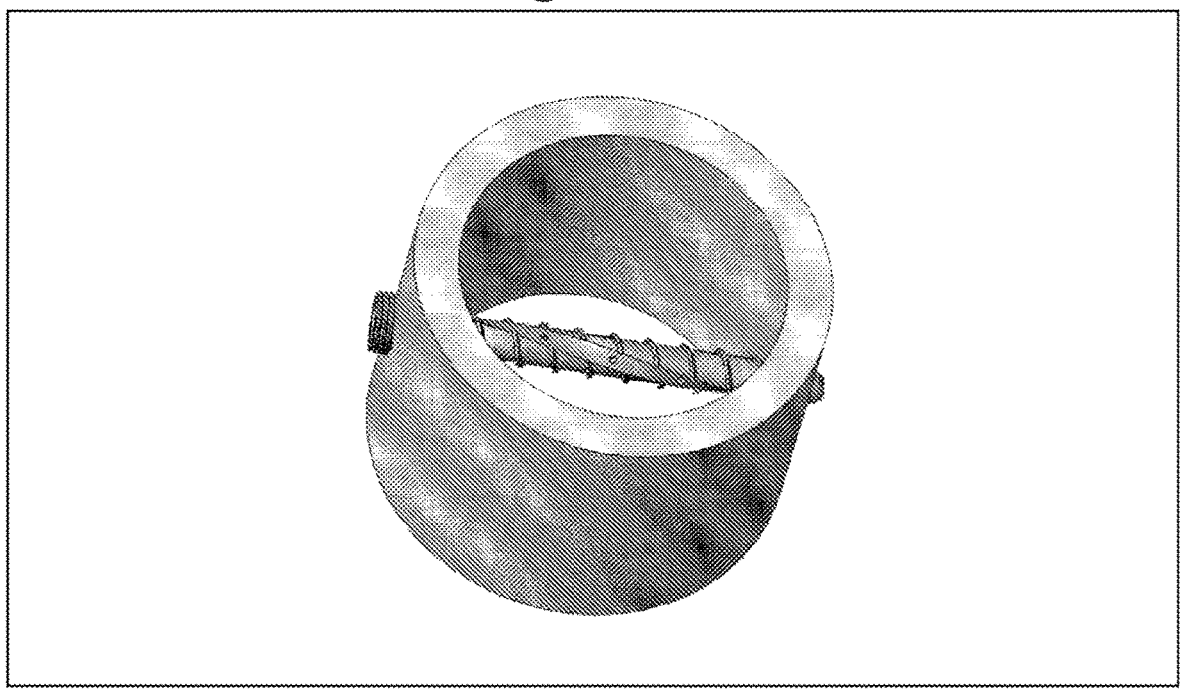
FIG. 18B is a side view of a bicortical insertion of a bone screw into a simulated cross-section of bone.

Alternatively, for bi-cortical fixation, the bone screw penetrates all the way through the bone and reaches the opposite thick cortical wall, as shown schematically in FIG. 18B. An exemplary bone screw for bi-cortical fixation is, e.g., 60-80 mm long, with, e.g., a 4.0 mm major diameter and, e.g., a 1.6 mm interior channel diameter.

In each instance, the exterior openings are located in the interior of the bone, where unsupported fragment sections may be held by cement injected therein. The bone screw includes a threaded head to which a delivery manifold, e.g., a disposable adaptor compatible with a disposable syringe, is directly attached to form an airtight seal. For example, a delivery manifold can be made of plastic and include a Luer fitting on one end for connection with syringes, and threading on the other end for connection to the screw head. To facilitate the surgery, the delivery manifold can be attached to the bone screw on the surgical table prior to insertion into the patient, rather than having to wait to connect the delivery manifold once the screw is in the bone, where it can become difficult to locate, align, and connect. In order to place the bone screw in position, a rotational driver is inserted through the delivery manifold, as shown in FIG. 7B, and engaged with the screw head.

When the screw is positioned appropriately, the rotational driver is removed, and a conventional syringe is attached. The syringe can be prepackaged to include an appropriate flowable medium, e.g., calcium phosphate bone cement, a saline solution used to irrigate the site prior to introduction of cement, an antibiotic, or a fibrinolytic agent used to prevent or disrupt clot formation; alternatively, the flowable medium can be introduced into an empty syringe. Upon attachment of the syringe, manual or "finger" pressure is then applied to the syringe to inject the flowable medium into the surgical site, e.g., the bone interior. The large total area of the exterior openings in relation to the cross-sectional area of the interior channel allows the surgeon or other user to apply only light pressure, which in turn minimizes the forces generated by advancing flowable medium and additionally minimizes the risk of tissue damage or air embolism. If surgically indicated, any flowable medium or other liquid at the surgical site can be withdrawn by pulling back on the syringe. The introduction and withdrawal of flowable medium or other liquid can be repeated as appropriate, using the same or a different syringe each time. In this manner, it is possible, for example, to irrigate thoroughly, apply an antibiotic or other appropriate biological agent, and then apply bone cement, all without needing to move the screw in or out of the surgical site.

Figure 18C:
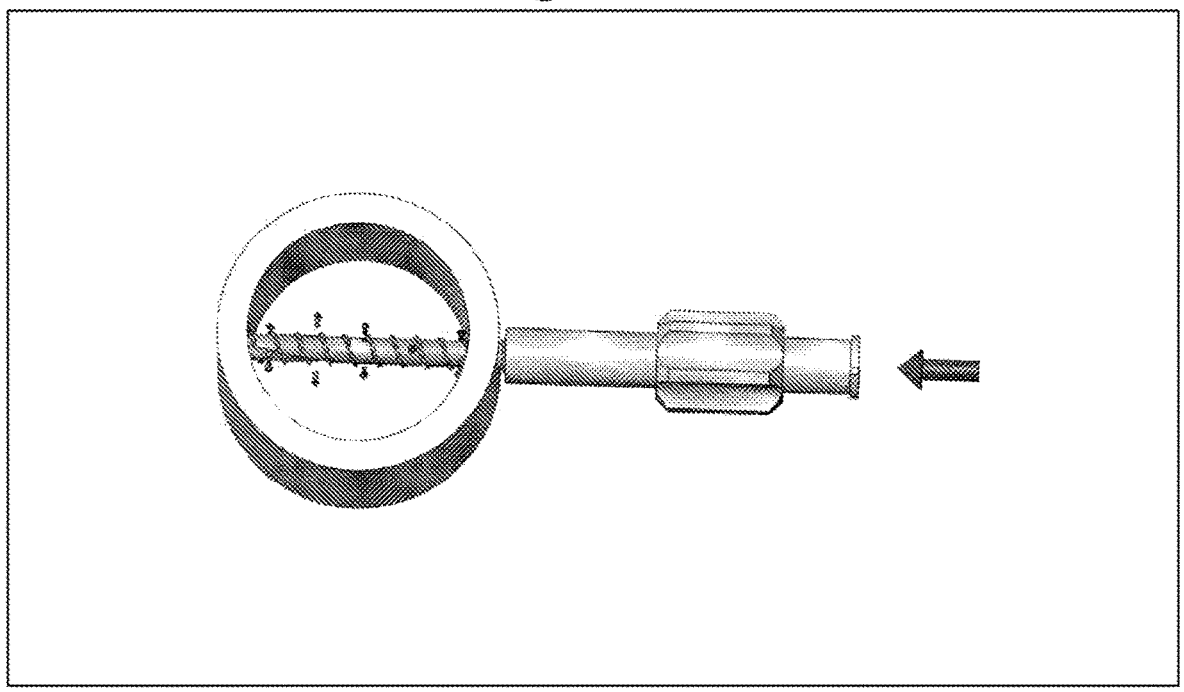
FIG. 18C is a side view of the bicortical bone screw insertion depicted in FIG. 18B, with a coupled Luer lock delivery manifold. Arrows show the flow path of flowable medium through the device.
Figure 19A:
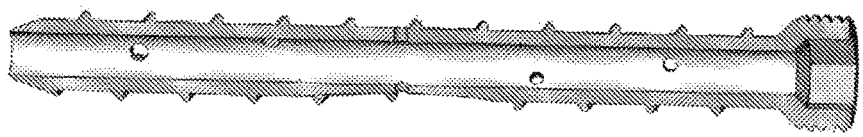
FIG. 19A is a sectional view of a bone screw that does not include a tip plug.
Figure 19B:
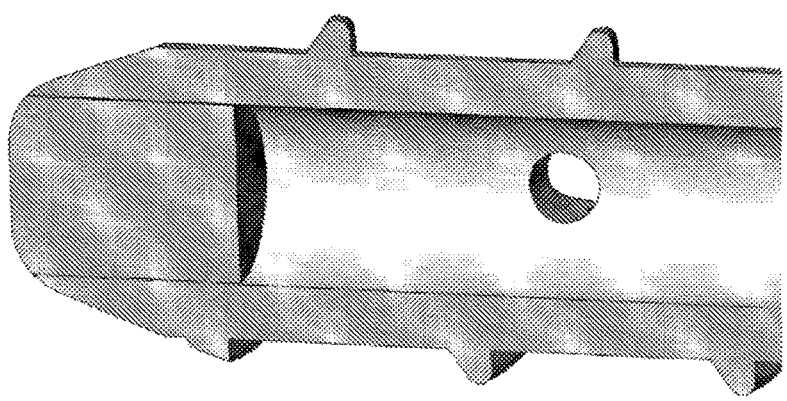
FIG. 19B is a sectional view of the tip of the bone screw of FIG. 19A, with a tip plug inserted.
Figure 20A:
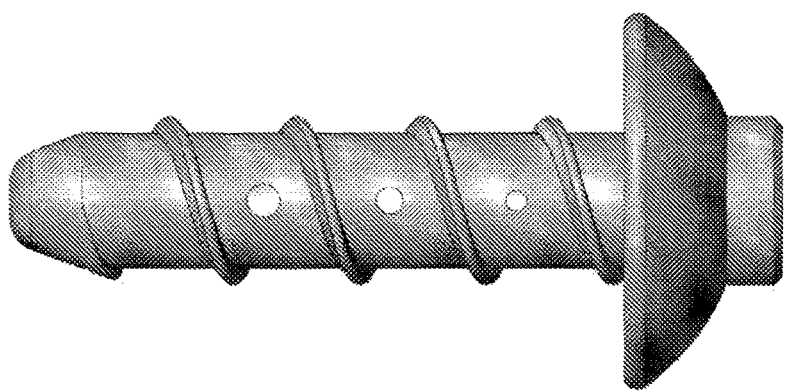
FIG. 20A is a side view of a bone screw that is optimized for dental applications. The bone screw includes an integral cap attached to the head. The cap can be used to prevent the flow of a flowable medium or biological material, once extruded through the delivery channels, to a position beyond the screw head.
Figure 20B:
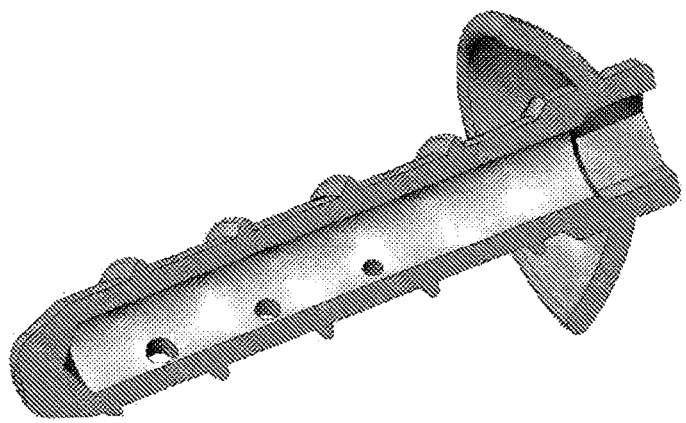
FIG. 20B is a sectional view of the bone screw of FIG. 20A.
Figure 20C:
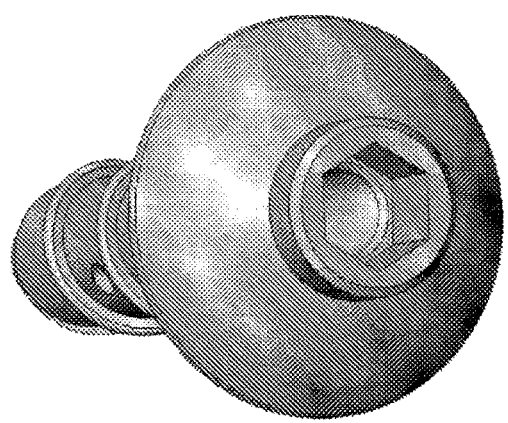
FIG. 20C is a top view of the bone screw of FIG. 20A.
Figure 20D:
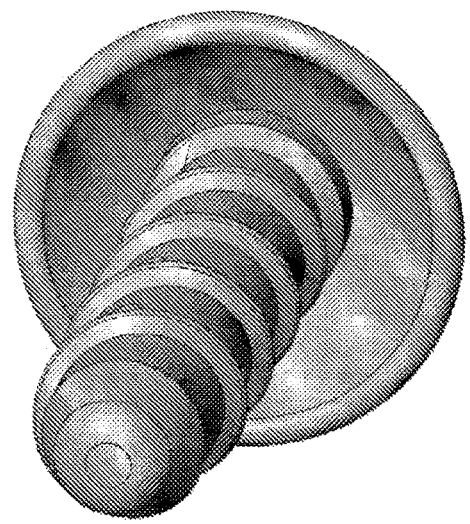
FIG. 20D is a bottom view of the bone screw of FIG. 20A.

A depiction of the flow path of the injected cement is shown in FIG. 18C.

Prevention of Terminal Extrusion

In some instances, it is undesirable to permit terminal extrusion of bone cement or other flowable medium from the tip of the screw distal to the screw head. Accordingly, in one embodiment, a bone screw is not fully cannulated, i.e., the interior channel does not extend all the way through the tip. In some surgical contexts, however, e.g., osteoporotic hip fracture, it is desirable to use a fully cannulated screw, e.g., in order to allow for the use of a guide wire to place the screw prior to filling and extrusion of flowable medium. In such instances, following placement of the bone screw in the surgical site, a solid internal plug is pushed through the interior channel to the tip. The bone screw is designed to have a narrowed tip so that the plug wedges into place and is not released from the screw. Following insertion of the plug, bone cement or other flowable medium is loaded into the screw, and the flowable medium is extruded through the delivery channels but not through the tip. Having the ability to plug the tip of a fully cannulated bone screw significantly increases safety and flexibility of use, e.g., in situations in which injection of bone cement into soft tissue outside the bone, e.g., a joint, would be problematic or even catastrophic.

Example 2: Use of a Bone Screw of the Invention to Facilitate Dental Implant

A blind hole created during tooth replacement often requires a bone graft in order to provide support for the post of a dental implant. A bone screw of the invention can be used to facilitate placement of such an implant. As shown in FIGS. 20A-20D, a bone screw optimized for dental applications contains a curved cap affixed to the screw head. For example, the bone screw can have an interior channel diameter of 1.0-2.0 mm, e.g., 1.2 mm, and a major diameter of 3.0-5.0 mm, e.g., 3.0 mm.

The bone screw is first inserted into, e.g., the maxilla or mandible, and bone cement or other flowable medium is injected and evenly distributed along the axis of the hole. The curved cap is shaped to contain the flowable medium. The cement can act to rebuild the lost bone stock, which allows for increased height of bone anchorage and permits sufficient stability for subsequent insertion of a dental implant over the bone screw.

In an alternative dental implant procedure, a bone screw of the invention can be inserted into a hole in the maxilla or mandible as a temporary measure, allowing new bone to grow in. Once bone growth has occurred, the bone screw is removed, and a conventional dental implant is inserted into the augmented bone site.

Example 3: Use of a Bone Screw of the Invention to Repair Fractures Near Joints that are Reconstructed but do not have Enough Load-Bearing Strength with Conventional Fixation Alone A patient presents with a fracture of the tibia or femur occurring near the tibial-femoral or tibial-talar joint. For example, in a high-speed automobile collision, the femur just above the knee can break when the crash victim's bent leg hits the dashboard. The bone may break into two, three, or more pieces. The site to be repaired can be accessed using a percutaneous or open technique. The small profile of cement connection means the screw and cement can be done with a wide incision (open) or with a very small incision (closed).

By using a bone screw of the invention, subsequent screw removal is possible while ensuring maximal bone conservation. For example, a screw designed for use with an interior rotational driver, e.g., an internal hex driver, eliminates the need to use a large external driver, e.g., a wrench. Because healing bone grows up and around the head of a screw that has been inserted into a surgical site, insertion of a large tool is difficult and would result in significant bone loss or damage to adjacent bone. Integration of the interior channel and screw head rotational driver opening allows use of a small drill or pick to remove a small amount of bone directly over the screw head and insertion of a rotational driver to pull out the screw with minimal effect on adjacent bone.

Alternatively, in an embodiment in which the screw head is not significantly larger than the screw body, a cannulated chamfer can be drilled over the screw, and the friction generated thereby allows extraction of the screw with minimal bone loss. In this configuration, for screws having spiral exterior grooves, the torque necessary to extract the screw prior to setting of the bone cement is reduced significantly (e.g., by 10%, 20%, 30%, 33%, 40%, 50%, or more, e.g., from about 3 Newton meters to about 2 Newton meters) relative to prior art screws. In contrast, after setting of the bone cement, the force needed to extract the bone screw of the invention is significantly increased relative to prior art screws (e.g., by a factor of 1.1, 1.2, 1.5, 2.0, 2.5, 3.0, 4.0, 5.0, 6.0, 7.5, or even 10.0, e.g., from about 300 Newtons to about 1,600-1,800 Newtons).

Example 4: Use of a Bone Screw of the Invention to Repair a Contralateral Defect Where a contralateral defect is present, e.g., in metaphyseal bone, a bone screw of the invention can be inserted opposite the defect, so that the screw tip is positioned close to the defect. Next, flowable medium is injected at the site of the defect. By inserting the bone screw opposite the defect rather than through it, damage to the blood supply on the defect side of the bone is avoided, and a second incision for grafting cement or other biological material is not needed.

Example 5: Use of a Bone Screw of the Invention in Conjunction with Other Internal Fixation Devices Bone screws of the invention can be used in conjunction with other internal fixation devices such as plates, including locking plates, and nails. The screw is constructed so that it can be inserted through one or more of the existing holes in the plate or nail without weakening the plate or nail construct. This technique is particularly useful in the contexts of bone comminution or osteoporotic bone, where the structure of the bone may be too fragile to allow a conventional screw to obtain stable purchase in the weakened bone site or successfully fasten the plate or nail to the weakened bone site, and if the hole in the plate or nail were left empty, it would result in a stress riser in the plate or nail. In such an instance, a bone screw of the invention is inserted into the hole, bone cement is injected and distributed uniformly around the axis of the screw, and the bone cement is allowed to harden, fixing the plate or nail to the bone.

Figure 16A:
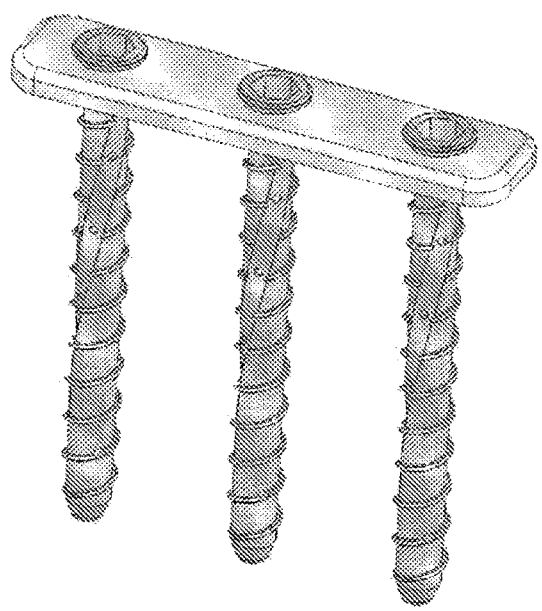
FIG. 16A is a side view of a bone plate with three bone screws inserted.
Figure 16B:
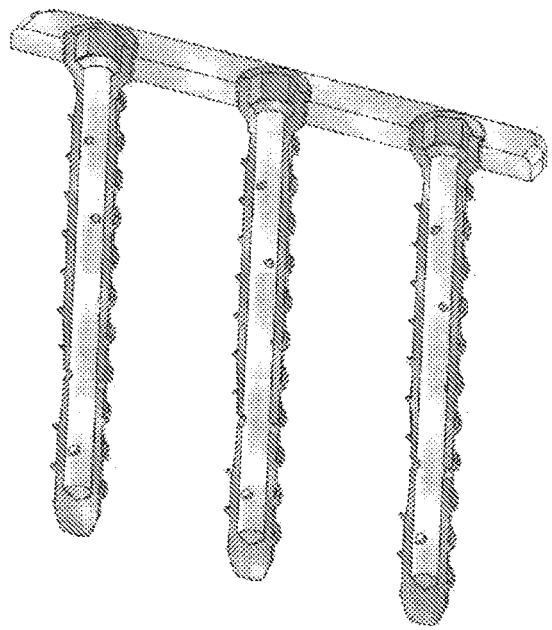
FIG. 16B is a sectional view of the bone plate and bone screws of FIG. 16A.
Figure 16C:
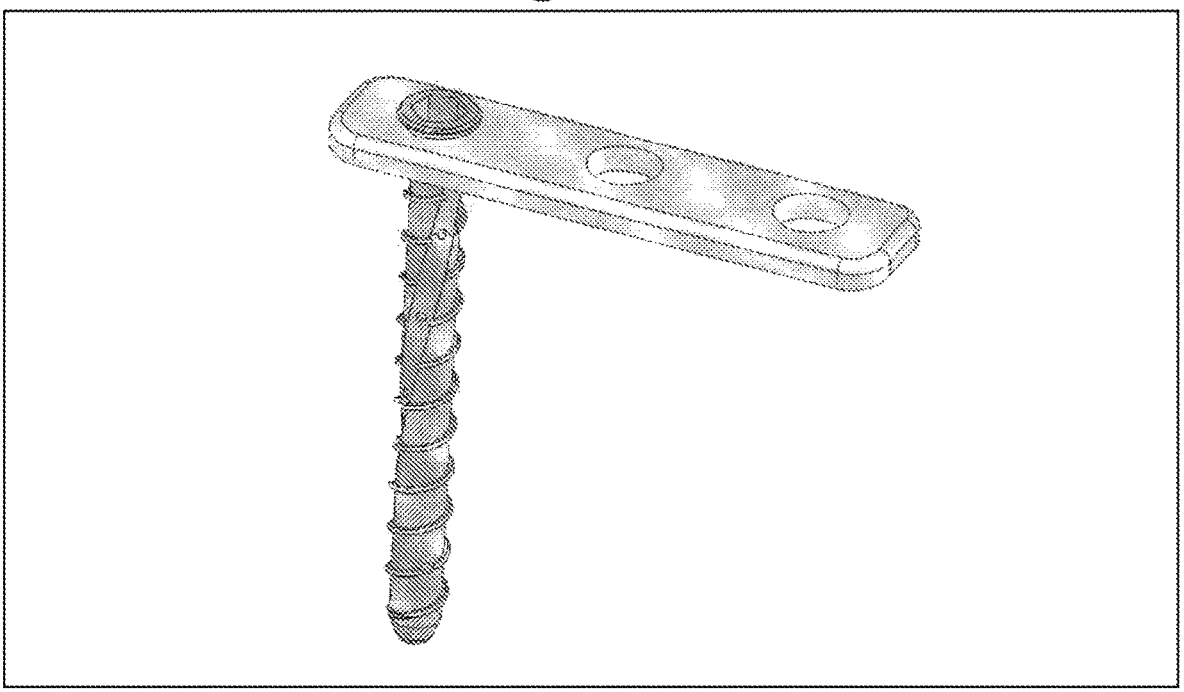
FIG. 16C is a side view of a bone plate with one hole occupied by a bone screw and two holes unoccupied.

For example, FIGS. 16A-16C depict bone screws of the invention inserted into a bone plate designed to receive three locking screws. Bone screws of the invention can be used in all three holes, or can be used for only one or two of the holes, depending on the surgical procedure and the quality of the bone site.

In some instances, bone screws of the invention can be used in revision surgeries, in which prior art screws or plates exhibit loosening or weakening over time. Replacing a prior art screw with a screw of the present invention can provide greater stability and reinforcement.

Example 6: Use of a Bone Screw of the Invention in Conjunction with Reattachment of Ligaments or Tendons In situations requiring reattachment of ligaments or tendons, there is a risk that sutures may pull out of the attaching bone. Suture anchors, e.g., washer-type devices, are known in the art, but such anchors may also be displaced if the bone quality is inadequate. A suture anchor can be attached to a bone screw of the present invention, as shown, e.g., in FIGS. 15A-15D, and the bone screw can be firmly cemented into a bone site that might otherwise be too weak or comminuted to secure a conventional bone screw.

Figure 17A:
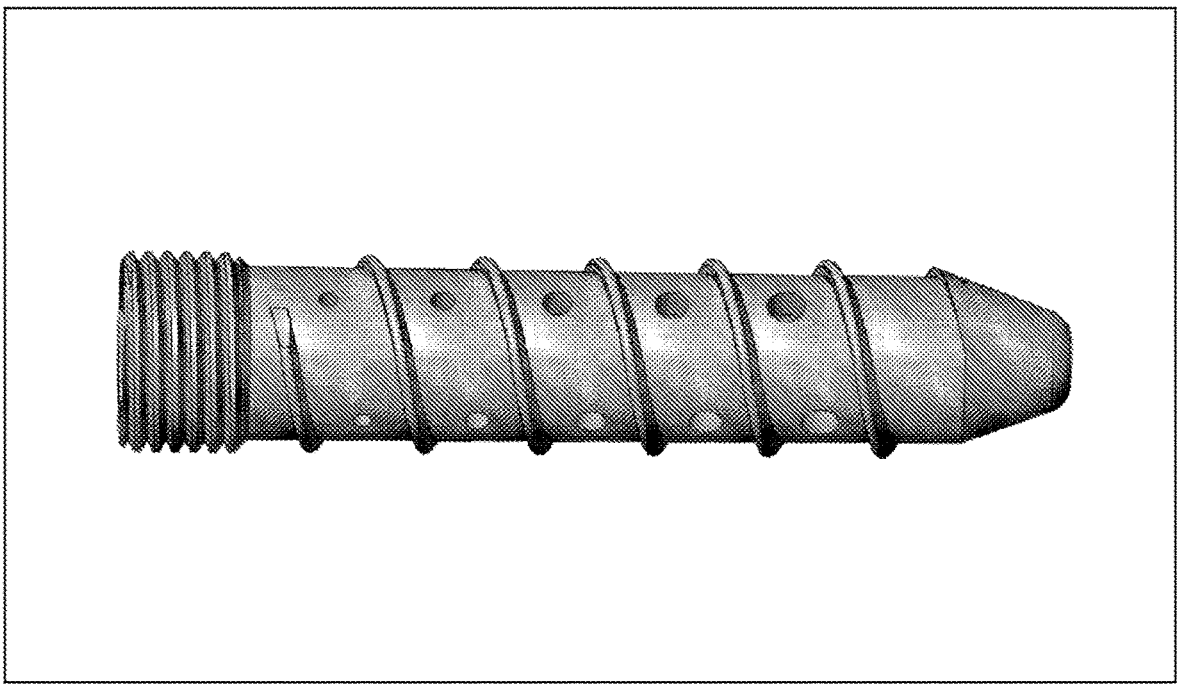
FIG. 17A is a side view of a bone screw optimized for anterior cruciate ligament reconstruction. In the depicted embodiment, the diameter of the screw head is substantially the same as the diameter of the screw body, facilitating full insertion of the bone screw, including insertion of the screw head. In an embodiment, the length of the screw body can be, e.g., 15-40 mm, the major diameter can be, e.g., 6.0-12.0 mm, and the diameter of the interior channel can be, e.g., 1.0-5.0 mm.
Figure 17B:
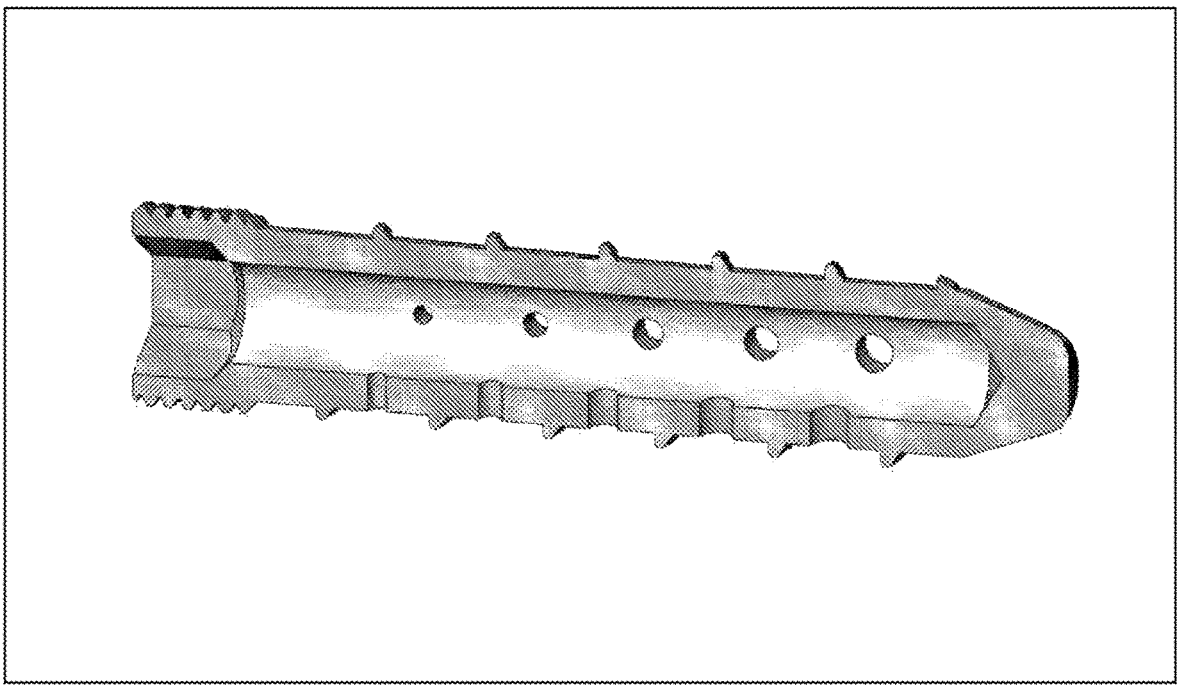
FIG. 17B is a sectional view of the bone screw of FIG. 17A.
Figure 17C:
FIG. 17C is a diagonal view of the bone screw of FIG. 17A.

Example 7: Use of a Bone Screw of the Invention for Anterior Cruciate Ligament (ACL) Reconstruction Bone screws of the present invention can be used to position and anchor replacement of the ACL following a tear. A hole is drilled in the bone at each end, and a graft is placed where the ACL should be. The graft is generally longer than the ACL. The screws can be used to hold the graft to the bone. In bone screws of the invention for which the diameter of the screw head is substantially the same as the diameter of the screw body, e.g., the bone screws depicted in FIGS. 17A-17C, the screw head can readily be sunk within the graft and/or bone by using a rotational driver inserted inside the screw head, thereby facilitating the ACL reconstruction.

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A fenestrated bone screw, comprising:
a cylindrical screw body extending from a proximal end to a distal end along a longitudinal axis, the screw body including a helical thread disposed at a first angular orientation relative to the longitudinal axis of the screw body;
a screw head disposed at the proximal end of the screw body;
an interior channel extending longitudinally through the screw head and through at least a portion of the screw body; and
a plurality of radially-disposed delivery channels extending from the interior channel to an exterior surface of the screw body, the delivery channels helically aligned along the screw body and disposed at a second angular orientation relative to the longitudinal axis of the screw body that is different from the first angular orientation of the helical thread,
wherein the plurality of radially-disposed delivery channels are distributed in two helical arrays offset by 180 degrees with pairs of delivery channels positioned directly opposite each other across the screw body, wherein each radially disposed delivery channel of the plurality of radially disposed delivery channels is radially offset such that an axis intersecting any portion of an outer periphery of each radially disposed delivery channel does not intersect with any portion of any adjacent radially disposed delivery channel, wherein the axis runs parallel to the longitudinal axis of the screw body, and
wherein each helical array of the two helical arrays is disposed within a helical groove that interrupts the helical thread, extends from the proximal end to the distal end in the exterior surface of the screw body and wraps 180 degrees around the screw body.

2. The fenestrated bone screw of claim 1, wherein a diameter of the interior channel is less than 5 mm.

3. The fenestrated bone screw of claim 1, wherein the distal end of the screw body includes an opening in fluid communication with the interior channel.

4. The fenestrated bone screw of claim 1, wherein diameters of the delivery channels progressively increase from the proximal end of the screw body toward the distal end of the screw body.

5. The fenestrated bone screw of claim 1, wherein the interior channel includes a first interior channel portion defined by a first diameter and a second interior channel portion defined by a second diameter, the second diameter less than the first diameter.

6. The fenestrated bone screw of claim 5, wherein the second interior channel portion is disposed closer to the distal end of the screw body than the first interior channel portion.

7. The fenestrated bone screw of claim 1, wherein the delivery channels are disposed between adjacent crests of the helical thread.

8. The fenestrated bone screw of claim 1, wherein the delivery channels are sized to generate substantially equal flow rates of a flowable medium extruded through each delivery channel following introduction of the flowable medium through the screw head into the interior channel.

9. A fenestrated bone screw, comprising:
a cylindrical screw body extending from a proximal end to a distal end along a longitudinal axis, the screw body including a helical thread extending from an exterior surface of the screw body and wrapping around the longitudinal axis of the screw body;
a screw head disposed at the proximal end of the screw body;
an interior channel extending longitudinally through the screw body from a proximal opening in the proximal end to a distal opening in the distal end; and
a plurality of delivery channels disposed between adjacent crests of the helical thread and extending from the interior channel to the exterior surface of the screw body, wherein the delivery channels are disposed in a nonlinear arrangement along a length of the screw body where each successive delivery channel is shifted around a circumference of the screw body such that an axis intersecting any portion of an outer periphery of each delivery channel does not intersect with any portion of neighboring delivery channels, wherein the axis runs parallel to the longitudinal axis of the screw body,
wherein the nonlinear arrangement is disposed within a helical groove, and the helical groove extends from the proximal end to the distal end while wrapping around 180 degrees of the circumference of the cylindrical screw body and the helical groove including a different pitch than the helical thread and interrupting the helical thread.

10. The fenestrated bone screw of claim 9, wherein the helical thread extends from a location adjacent to the screw head to a location adjacent to the distal end of the screw body.

11. The fenestrated bone screw of claim 9, wherein the nonlinear arrangement of the delivery channels comprises a helical pattern.

12. The fenestrated bone screw of claim 11, wherein the delivery channels become progressively larger from the proximal end of the screw body to the distal end of the screw body.

13. The fenestrated bone screw of claim 12, wherein a diameter of the interior channel varies along the length of the screw body.

14. The fenestrated bone screw of claim 13, wherein the delivery channels are sized to generate substantially equal flow rates of a flowable medium extruded through each delivery channel following introduction of the flowable medium through the screw head into the interior channel.

15. A fenestrated bone screw, comprising:
a cylindrical screw body extending from a proximal end to a distal end along a longitudinal axis, the screw body including a helical thread extending in a first direction;
a screw head disposed at the proximal end of the screw body;

an interior channel extending longitudinally through the screw head and through at least a portion of the screw body; and a plurality of radially-disposed delivery channels extending from the interior channel to an exterior surface of the screw body, the delivery channels helically aligned along the screw body in a helical pattern wrapping around the circumference of the screw body such that an axis intersecting any portion of an outer periphery of each delivery channel does not intersect with any portion of neighboring delivery channels, wherein the axis runs parallel to the longitudinal axis of the screw body, wherein each radially-disposed delivery channel of the plurality of radially-disposed delivery channels is helically aligned along the screw body such that axes extending along the longitudinal axis of the screw from the periphery of each radially-disposed delivery channel do not intersect with an adjacent radially-disposed delivery channel, wherein the helical pattern is disposed within a helical groove, and the helical groove extends from the proximal end to the distal end while wrapping around 180 degrees of the circumference of the cylindrical screw body and the helical groove including a different pitch than the helical thread and interrupting the helical thread.

16. The fenestrated bone screw of claim 15, wherein the delivery channels are disposed between the helical thread along the screw body without interrupting the helical thread.

17. The fenestrated bone screw of claim 16, wherein the delivery channels become progressively larger from the proximal end of the screw body to the distal end of the screw body.

18. The fenestrated bone screw of claim 17, wherein a diameter of the interior channel tapers between the proximal end of the screw body and the distal end of the screw body.

* * * * *